United States Patent
Bagrov et al.

(10) Patent No.: US 8,038,997 B2
(45) Date of Patent: Oct. 18, 2011

(54) ANTI-MARINOBUFAGENIN ANTIBODIES AND METHODS FOR THEIR USE

(75) Inventors: Alexei Bagrov, Bel Air, MD (US); Olga V. Fedorova, Bel Air, MD (US); Edward G. Lakatta, Bel Air, MD (US); Andrey Simbirtsev, St. Petersburg (RU); Alexander Kotov, St. Petersburg (RU); Nikolai Kolodkin, St. Petersburg (RU)

(73) Assignee: The United States of America as represented by the Secretary of the Department of Health and Human Services, Washington, DC (US)

( * ) Notice: Subject to any disclaimer, the term of this patent is extended or adjusted under 35 U.S.C. 154(b) by 935 days.

(21) Appl. No.: 11/993,309

(22) PCT Filed: Jun. 26, 2006

(86) PCT No.: PCT/US2006/024918
§ 371 (c)(1),
(2), (4) Date: Dec. 20, 2007

(87) PCT Pub. No.: WO2007/002638
PCT Pub. Date: Jan. 4, 2007

(65) Prior Publication Data
US 2010/0158900 A1    Jun. 24, 2010

Related U.S. Application Data

(60) Provisional application No. 60/694,733, filed on Jun. 27, 2005.

(51) Int. Cl.
*A61K 39/395* (2006.01)
*C07K 16/00* (2006.01)
*C07K 16/26* (2006.01)
*G01N 33/53* (2006.01)

(52) U.S. Cl. ............... 424/145.1; 424/130.1; 424/133.1; 424/141.1; 424/152.1; 424/172.1; 435/7.2; 530/387.1; 530/387.3; 530/388.1; 530/388.2; 530/388.24

(58) Field of Classification Search ................ None
See application file for complete search history.

(56) References Cited

U.S. PATENT DOCUMENTS

| | | | |
|---|---|---|---|
| 5,770,376 A | 6/1998 | Bagrov | |
| 2004/0018201 A1 | 1/2004 | Adair | |
| 2004/0018202 A1 | 1/2004 | Adair | |

FOREIGN PATENT DOCUMENTS

| | | |
|---|---|---|
| WO | 2004/011028 | 2/2004 |
| WO | 2004/071273 | 8/2004 |

OTHER PUBLICATIONS

The Merck Manual of Medical Diagnosis and Therapy, Seventeenth Edition edited by Beers et al., Merck Research Laboratories, Whitehouse Station, NJ 1999; pp. 1629-1648; 2057-2058.*
Fedorova et al., J Hypertens 26: 2414-2425, 2008.*
Kolmakova et al., Nephrol Dial Transplant Feb. 2011 [Epub ahead of print] PubMed PMID: 21292813.*
Tian et al., Hypertension 56(5): 914-919, 2010.*
Nikitina et al., J Hypertens Feb. 16, 2011 [Epub ahead of print] PubMed PMID: 21330936.*
Bagrov et al., "Antiarrhythmic Effect of Antibodies to Digoxin in Acute Myocardial Ischemia in Rats," *European Journal of Pharmacology*, 162:195-196, 1989.
Fedorova et al., "Antibody to Marinobufagenin Lowers Blood Pressure in Pregnant Rats on a High NaCl Intake," *Journal of Hypertension*, 23(4):835-842, Apr. 2005, abstract.
Fedorova et al., "Endogenous Ligand of Alpha1 Sodium Pump, Marinobufagenin, Is a Novel Mediator of Sodium Chloride-Dependent Hypertension," *Circulation*, 105(9):1122-1127, Mar. 2002, abstract.
Goodlin, Robert C., M.D., "Antidigoxin Antibodies in Eclampsia," *The New England Journal of Medicine*, pp. 518-519, 1988.
Kennedy et al., "Hypertension: Central Role for the Cardiotonic Steroid Marinobufagenin in the Pathogenesis of Experimental Uremic Cardiomyopathy," *Journal of the American Heart Association*, pp. 488-495, 2006.
Lopatin et al., "Circulating Bufodienolide and Cardenolide Sodium Pump Inhibitors in Preeclampsia," *Journal of Hypertension*, 17(8):1179-1187, Aug. 1999.
Menezes et al., "Digoxin Antibody Decreases Natriuresis and Diuresis in Cerebral Hemorrhage," *Intensive Care Med*, 29:2291-2296, 2003.
Schoner, Wilhelm, "Endogenous Cardiac Glycosides, A New Class of Steroid Hormones," *Eur. J. Biochem*, 269:2440-2448, 2002.
Steyn et al., "Bufadienolides of Plant and Animal Origin," *Natural Product Reports*, pp. 397-413, 1998.

* cited by examiner

*Primary Examiner* — Phillip Gambel
(74) *Attorney, Agent, or Firm* — Klarquist Sparkman, LLP

(57) ABSTRACT

Described herein are deposited hybridoma cell lines and the monoclonal antibodies produced by these hybridomas, and antigen binding fragments thereof. These monoclonal antibodies and antigen binding fragments specifically bind marinobufagenin. The disclosure also encompasses the use of these monoclonal antibodies or antigen binding fragments in a method for detecting the presence of marinobufagenin in a biological sample. Also provided are methods for the use of these monoclonal antibodies or antigen binding fragments as prophylactic, therapeutic, and diagnostic agents for the detection, inhibition and treatment of a cardiovascular disease, for example, essential hypertension, hypertension associated with preeclampsia, eclampsia, or renal failure, or myocardial fibrosis in a subject.

57 Claims, 1 Drawing Sheet

ANTI-MARINOBUFAGENIN ANTIBODIES AND METHODS FOR THEIR USE

CROSS REFERENCE TO RELATED APPLICATION

This is the U.S. National Stage of International Application No. PCT/US 2006/024918, filed Jun. 26, 2006, which was published in English under PCT Article 21(2), which in turn claims the benefit of U.S. Provisional Application No. 60/694,733, filed Jun. 27, 2005, which is incorporated herein in its entirety.

FIELD

This disclosure relates to the field of antibodies, specifically to antibodies (mAbs) that specifically bind marinobufagenin (MBG) and the use of these mAbs in the diagnosis and treatment of cardiovascular disease such as hypertension.

BACKGROUND

Hypertension is a condition characterized by persistent high arterial blood pressure (BP). Hypertension may have no known cause (essential or idiopathic hypertension) or may be associated with other primary diseases (secondary hypertension), and is considered a risk factor for the development of heart disease, peripheral vascular disease, stroke, and kidney disease.

Preeclampsia is a rapidly progressive condition occurring during pregnancy characterized by high BP, edema, and protein in the urine. Preeclampsia is the presence of pregnancy-induced hypertension, accompanied by proteinuria, edema or both, after 20 weeks of fetal gestation. Preeclampsia occurs in 5 to 10 percent of all pregnancies and is most common in first-time pregnancies. Complications of preeclampsia include eclampsia, characterized by convulsions and coma, and intrauterine fetal demise. While the cause(s) of preeclampsia and eclampsia are not fully elucidated, several theories have been put forth. One theory proposes that elevated serum levels of digitalis-like sodium pump ligands (SPLs), which act as $Na^+/K^+$-ATPase enzyme inhibitors, play a central role in the increased peripheral vasoconstriction exhibited in preeclampsia. This is thought to be mediated through ion exchange pumps resulting in increased intracellular calcium, which promotes vasoconstriction and resultant hypertension (Hamlyn et al., Fed. Proc. 44:2782-88, 1985).

Chronic renal failure is complicated by the propensity of subjects to develop cardiovascular diseases such as hypertension and uremic cardiomyopathy. Cardiac disease is directly responsible for much of the morbidity and mortality seen in patients with end-stage renal disease (Sartank et al., Circulation 108:2154-2169, 2003). Cardiomyopathy is a disorder of the heart muscle that often leads to myocardial dysfunction, such as hypertrophy, diminished contractility, and reduced pump function. Uremic cardiomyopathy is characterized by a systemic oxidant stress state, marked cardiac hypertrophy, and diastolic dysfunction. Even mild degrees of chronic renal failure confer a significant increase in cardiovascular disease (Garg et al., Kidney Int. 61:1486-1494, 2002). Cardiac myocytes isolated from rats subjected to partial (ie, five-sixth) nephrectomy have diastolic dysfunction in vitro, which can be attributed to reduced sarcoplasmic reticulum calcium ATPase (SERCA) activity and, in turn, appears to be dependent on proportional decreases in SERCA2a protein and mRNA (Kennedy et al., J. Am. Soc. Nephrol. 14:90-97, 2003). Steroid molecules, which bind to the plasmalemmal $Na^+/K^+$-ATPase and have structural similarity to the digitalis-like sodium pump ligands (SPLs), accumulate in renal failure.

Bufadienolides, which were discovered in amphibians, inhibit $Na^+/K^+$-ATPase activity and cross-react with digitalis antibodies (Flier et al., Science 208:503-05, 1980). Several bufadienolides have been suggested as candidate SPLs in mammals, including MBG, which acts in vitro as a vasoconstrictor (Fedorova et al., Am. J. Hypertens. 10:929-35, 1997 and Lopatin et al., J. Hypertens. 17:1179-87, 1999). Marinobufagenin immunoreactive material purified from human urine is identical to MBG from the toad, Bufo marinus. Enhanced MBG production occurs in pathological states associated with fluid retention, including essential and salt-sensitive hypertension, preeclampsia and uremic cardiomyopathy (Gonick et al, Clin. Exp. Hypertens. 1998; 20: 617-627, Bagrov et al., Hypertension 31:1097-1103, 1998; Fedorova et al., Hypertension 37:462-66, 2001; and Lopatin et al., J. Hypertens. 17:1179-87, 1999, Fedorova et al, Circulation 2002; 105: 1122-1127, Kennedy et al., Hypertension 47:448-495, 2006).

SUMMARY

The present disclosure relates to antibodies, including mAbs and antigen binding fragments, that specifically bind MBG.

In one embodiment of the disclosure, a method is disclosed for the use of mAbs or antigen binding fragments that specifically bind MBG for detecting the presence of MBG in a biological sample.

In several of the embodiments of the disclosure, methods are disclosed for exposing a subject to anti-MBG antibodies in an amount sufficient to treat a cardiovascular condition, such as hypertension. The subject may be exposed to the anti-MBG mAbs or antigen binding fragments that specifically bind MBG. The mAbs may be used as prophylactic, therapeutic, or diagnostic agents for the detection, inhibition and treatment of cardiovascular conditions. Disclosed examples of such conditions include myocardial fibrosis and hypertension, such as essential hypertension, hypertension associated with preeclampsia, eclampsia and uremic cardiomyopathy. In certain disclosed embodiments these benefits are achieved by immunization of subjects with MBG.

The foregoing and other features and advantages will become more apparent from the following detailed description of several embodiments, which proceeds with reference to the accompanying FIGURE.

DETAILED DESCRIPTION

I. Abbreviations

Figure 1:
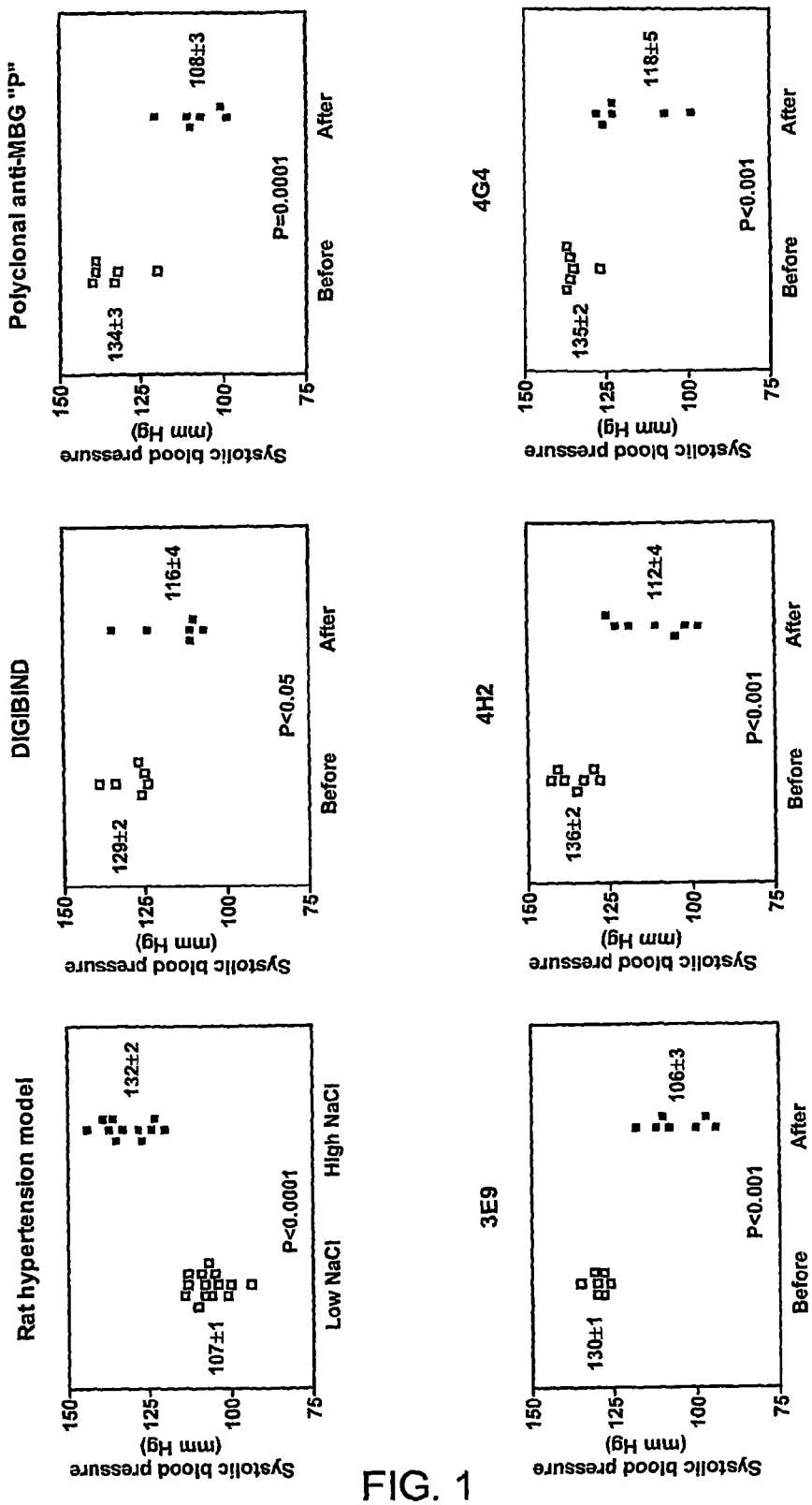
FIG. 1 is a scattergram showing the in vivo effects of the 3E9, 4G4 and 4H2 mAbs on blood pressure in rats with pregnancy-associated hypertension. The effect of DIGIBIND and a polyclonal anti-MBG antibody are also shown.

| | |
|---|---|
| Ab: | antibody |
| BP: | blood pressure |
| BSA: | bovine serum albumin |
| DIGIBIND: | affinity-purified ovine digoxin antibody Fab fragments |
| DMM: | Davis minimal medium |
| DS: | Dahl salt-sensitive rats |

-continued

| I. Abbreviations | |
|---|---|
| ELISA: | enzyme-linked immunoabsorbent assay |
| FCS: | fetal calf serum |
| HAT: | hypoxanthine, aminopterin, thymidine |
| HS: | high salt |
| IFA: | indirect immuno-fluorescence assay |
| mAb: | monoclonal antibody |
| MBG: | marinobufagenin |
| NaCl: | sodium chloride |
| $Na^+/K^+$: | sodium/potassium |
| PE: | preeclampsia |
| PEG: | polyethylene glycol |
| RIA: | radioimmunoassay |
| SBP: | systolic blood pressure |
| SPLs: | digitalis-like sodium pump ligands |

II. Terms

Unless otherwise noted, technical terms are used according to conventional usage. Definitions of common terms in molecular biology may be found in Benjamin Lewin, *Genes VII*, published by Oxford University Press, 2000 (ISBN 019879276X); Kendrew et al. (eds.), *The Encyclopedia of Molecular Biology*, published by Blackwell Publishers, 1994 (ISBN 0632021829); and Robert A. Meyers (ed.), *Molecular Biology and Biotechnology: a Comprehensive Desk Reference*, published by Wiley, John & Sons, Inc., 1995 (ISBN 0471186341); and other similar references.

In order to facilitate review of the various embodiments of this disclosure, the following explanations of specific terms are provided:

Animal: Living multi-cellular vertebrate organisms, a category that includes, for example, mammals and birds. The term mammal includes both human and non-human mammals. Similarly, the term "subject" includes both human and veterinary subjects, for example, humans, non-human primates, dogs, cats, horses, and cows.

Antibody: A protein (or protein complex) that includes one or more polypeptides substantially encoded by immunoglobulin genes or fragments of immunoglobulin genes. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

The basic immunoglobulin (antibody) structural unit is generally a tetramer. Each tetramer is composed of two identical pairs of polypeptide chains, each pair having one "light" (about 25 kDa) and one "heavy" (about 50-70 kDa) chain. The N-terminus of each chain defines a variable region of about 100 to 110 or more amino acids primarily responsible for antigen recognition. The terms "variable light chain" ($V_L$) and "variable heavy chain" ($V_H$) refer, respectively, to these light and heavy chains.

As used herein, the term "antibody" includes intact immunoglobulins as well as a number of well-characterized fragments. For instance, Fabs, Fvs, and single-chain Fvs (SCFvs) that bind to target protein (or epitope within a protein or fusion protein) would also be specific binding agents for that protein (or epitope). These antibody fragments are as follows: (1) Fab, the fragment which contains a monovalent antigen-binding fragment of an antibody molecule produced by digestion of whole antibody with the enzyme papain to yield an intact light chain and a portion of one heavy chain; (2) Fab', the fragment of an antibody molecule obtained by treating whole antibody with pepsin, followed by reduction, to yield an intact light chain and a portion of the heavy chain; two Fab' fragments are obtained per antibody molecule; (3) F(ab')$_2$, the fragment of an antibody obtained by treating whole antibody with the enzyme pepsin without subsequent reduction; F(ab')$_2$ is a dimer of two Fab' fragments held together by two disulfide bonds; (4) Fv, a genetically engineered fragment containing the variable region of a light chain and the variable region of a heavy chain expressed as two chains; and (5) single chain antibody (SCA), a genetically engineered molecule containing the variable region of a light chain and the variable region of a heavy chain, linked by a suitable polypeptide linker, as a genetically fused single chain molecule. Methods of making these fragments are routine (see, for example, Harlow and Lane, *Using Antibodies: A Laboratory Manual*, CSHL, New York, 1999).

"Chimeric antibodies" are antibodies whose light and heavy chain genes have been constructed, typically by genetic engineering, from immunoglobulin variable and constant region genes belonging to different species. For example, the variable segments of the genes from a mouse monoclonal antibody can be joined to human constant segments. In one example, a "therapeutic chimeric antibody" is thus a hybrid protein composed of the variable or antigen-binding domain from a mouse antibody and the constant or effector domain from a human antibody (although other mammalian species can be used); alternatively, the variable region can be produced by molecular biology techniques. Methods of making chimeric antibodies are well known in the art (see, for example, U.S. Pat. No. 5,807,715).

A chimeric antibody can be further "humanized" by replacing portions of the variable region not involved in antigen binding with equivalent portions from human variable regions. Methods of making humanized antibodies are routine (see, for example, Morrison, *Science* 229:1202-07, 1985). Such methods include isolating, manipulating, and expressing the nucleic acid sequences that encode all or part of an immunoglobulin variable region from at least one of a heavy or light chain. The cDNA encoding the humanized chimeric antibody, or fragment thereof, can then be cloned into an appropriate expression vector. Alternatively, suitable humanized antibodies can be produced by complementarity-determining region substitution (see, for example, U.S. Pat. No. 5,225,539).

Antibodies for use in the methods and compositions of this disclosure can be monoclonal or polyclonal. Specific, non-limiting examples of monoclonal antibodies include those mAbs produced by the 3E9, 4G4 and 4H2 hybridomas (referred to herein as the 3E9, 4G4 and 4H2 mAbs, respectively). Merely by way of example, monoclonal antibodies can be prepared from murine hybridomas according to the classical method of Kohler and Milstein (*Nature* 256:495-97, 1975) or derivative methods thereof. Detailed procedures for monoclonal antibody production are described in Harlow and Lane, *Using Antibodies: A Laboratory Manual*, CSHL, New York, 1999.

Antigen: A substance capable of inducing a specific humoral or cellular immune response and capable of reacting with the products of that response (that is, specific antibodies) or which can be bound by preformed antibodies. Those antigens capable of inducing antibody production are called "immunogens." Antigens can be soluble molecules such as proteins, lipids, carbohydrates, nucleic acids, or small molecules (for example, steroid hormones); or particulates such as bacteria, virus, or fungi, as whole cells, whole particles, or fragments thereof. Antigens can have complex surfaces and can express multiple unique antigenic determinants or epitopes. An antigen expressing different independent epitopes is said to be multi-determinant, while an antigen expressing multiple copies of a given epitope is said to be multivalent. In one embodiment, an antigen is a marinobufagenin antigen.

Avidity: The overall strength of interaction between two molecules, such as an antigen and an antibody. Avidity depends on both the affinity and the valency of interactions. Therefore, the avidity of a pentameric IgM antibody, with ten antigen binding sites, for a multivalent antigen may be much greater than the avidity of a dimeric IgG molecule for the same antigen.

Binding reaction: Occurs when a binding agent (such as an antibody) interacts with its target (such as an antigen). In some cases, a binding reaction occurs when two structurally and/or energetically complementary molecular surfaces react to form a ligand-receptor complex with characteristic specificity and affinity. For example, a monoclonal antibody can undergo a binding reaction with its cognate antigen to form an antigen-antibody complex, also called an immune complex. Thus, a binding reaction can be referred to as a "complexing reaction."

An agent that "selectively" binds to a particular target exhibits some preference for its target over other similar targets. Some antibodies (both monoclonal and polyclonal) can discriminate between closely related epitopes and also can distinguish between different antigens, if those antigens express epitopes that are not shared by other antigens. As one non-limiting example, the mAb produced by the 3E9 hybridoma reacts with an epitope that is found on MBG, but not on other bufadienolides or cardenolides (see Table I).

An agent that "specifically" binds to a particular target binds substantially only to a defined target. As used herein, a specific binding agent includes both monoclonal and polyclonal antibodies. Specific, non-limiting examples of monoclonal antibodies that bind substantially only to MBG include the 3E9, 404 and 4H2 mAbs.

cDNA (complementary DNA): A piece of DNA lacking internal, non-coding segments (introns) and regulatory sequences that determine transcription. cDNA is synthesized in the laboratory by reverse transcription from messenger RNA extracted from cells.

Cardiovascular Disease or Condition: A pathophysiological state of the cardiovascular system. The cardiovascular condition may be a primary disorder of the cardiovascular system (such as primary hypertension) or a secondary disorder (such as hypertension caused by renal failure). In particular examples disclosed herein, the pathophysiological state is associated with hypertension, such as essential hypertension hypertrophic cardiomyopathy, hypertension associated with pregnancy (as in preeclampsia or eclampsia) or renal disease (as in uremic cardiomyopathy)

Complementarity-determining region (CDR): The CDRs are three hypervariable regions within each of the variable light ($V_L$) and variable heavy ($V_H$) regions of an antibody molecule that form the antigen-binding surface that is complementary to the three-dimensional structure of the bound antigen. Proceeding from the N-terminus of a heavy or light chain, these complementarity-determining regions are denoted as "CDR1", "CDR2," and "CDR3," respectively. CDRs are involved in antigen-antibody binding, and the CDR3 includes a unique region specific for antigen-antibody binding. An antigen-binding site, therefore, may include six CDRs, comprising the CDR regions from each of a heavy and a light chain V region. Alteration of a single amino acid within a CDR region can destroy the affinity of an antibody for a specific antigen (see, for example, Abbas et al., *Cellular and Molecular Immunology*, 4th ed. 143-45, 2000). The locations of the CDRs have been precisely defined (see, for example, Kabat et al. (eds.), *Sequences of Proteins of Immunologic Interest*, National Institutes of Health, Bethesda, Md., NIH Publ. No. 91-3242, 1991).

Conjugate: A coupled molecular complex formed by conjugation. To "conjugate" refers to the covalent coupling of one molecule (for example, a mAb produced by the 3E9, 4G4 or 4H2 hybridomas) to another molecule (for example, a fluorochrome) or a small particle (for example, a colloidal gold particle). Another example of a "conjugate" is a conjugate formed by the conjugation of MBG with a carrier, such as a carrier protein, for example BSA. Such coupling may be achieved by chemical means, either with or without the use of a linking group.

Eclampsia: Convulsions and coma occurring in a pregnant subject; associated with preeclampsia (that is, with hypertension, edema, and/or proteinuria).

Epitope: An "antigenic determinant" or "antibody binding site." An epitope is any antigenic determinant on an antigen to which the paratope of an antibody binds. These are particular chemical groups, such as contiguous or non-contiguous peptide sequences, on a molecule that are antigenic, that is, that elicit a specific immune response. An antibody binds a particular antigenic determinant based on the three dimensional structure of the antibody and the matching (or cognate) three dimensional structure of the epitope.

Two antibodies are said to bind to the same epitope if each competitively inhibits (blocks) binding of the other to the antigen as measured in a competitive binding assay (see, for example, Junghans et al., *Cancer Res.* 50:1495-1502, 1990). Alternatively, two antibodies bind to the same epitope if amino acid mutations in the antigen that reduce or eliminate binding of one antibody reduce or eliminate binding of the other. Two antibodies are said to bind to overlapping epitopes if each partially inhibits binding of the other to the antigen, and/or if some amino acid mutations that reduce or eliminate binding of one antibody reduce or eliminate binding of the other.

Exposing a subject to anti-MBG antibodies: Exposing a subject to anti-MBG antibodies encompasses exogenous administration (for example, by exposing a subject to anti-MBG antibodies or anti-MBG mAbs, such as those produced by the 3E9, 4G4, and 4H2 hybridomas) or endogenous production of antibodies (for example, by immunization with MBG MBG conjugate, or an immunogenic fragment thereof).

Framework region (FR): Relatively conserved sequences flanking the three highly divergent CDRs within the variable regions of the heavy and light chains of an antibody. Hence, the variable region of an antibody heavy or light chain consists of a FR and three CDRs. Some FR residues may contact bound antigen; however, FRs are primarily responsible for folding the variable region into the antigen-binding site, particularly the FR residues directly adjacent to the CDRs. Without being bound by theory, the framework region of an antibody serves to position and align the CDRs. The sequences of the framework regions of different light or heavy chains are relatively conserved within a species. A "human" framework region is a framework region that is substantially identical (about 85% or more, usually 90-95% or more) to the framework region of a naturally occurring human immunoglobulin.

Hybridoma: A cell line or culture that secretes a homogenous population of monoclonal antibodies. Hybridomas are hybrid cells resulting from the fusion of a myeloma (tumor cell), which confers immortality, and an antibody-producing cell, which confers antibody specificity onto the hybridoma.

Specific, non-limiting examples are the 3E9, 4G4 and 4H2 hybridomas capable of producing mAbs to MBG. The 3E9 and 4G4 hybridomas were deposited on May 24, 2005 with the American Type Culture Collection (ATCC, Manassas, Va.) under ATCC accession numbers PTA-6724 and PTA-6725, respectively. The 4H2 hybridoma was deposited on Jun. 16, 2005 with the ATCC (Manassas, Va.) under ATCC accession number PTA-6788.

Hypertension: Elevated blood pressure associated with an increased risk of pathological effects. For example, sustained systolic blood pressure of greater than 140 and sustained diastolic blood pressure of greater than 90 are associated with adverse long-term cardiovascular sequelae.

Identifying characteristics: With regard to a hybridoma cell line, refers to the features which identify a particular hybridoma cell line. For example, the hybridoma cell lines described herein can be identified by the mAbs they produce. Accordingly, a hybridoma cell line having the identifying characteristics of a hybridoma cell line deposited on May 24, 2005 with the ATCC under ATCC accession number PTA-6724 (3E9 hybridoma) or PTA-6725 (4G4 hybridoma), or a hybridoma cell line having the identifying characteristics of a hybridoma cell line deposited on Jun. 16, 2005 with the ATCC under ATCC accession number PTA-6788 (4H2 hybridoma), will produce a mAb that is indistinguishable from that produced by the deposited hybridoma. Methods of determining if one antibody is indistinguishable from another antibody are well known in the art, and include, for example, comparison of cross-reactivities and competitive binding assays.

Inhibiting or treating a disease: Inhibiting the full development of a disease or condition, for example, in a subject who is at risk for a disease. Specific examples of diseases include cardiovascular diseases, such as essential hypertension, hypertension associated with preeclampsia, eclampsia, and renal failure. "Treatment" refers to a therapeutic intervention that ameliorates a sign or symptom of a disease or pathological condition after it has begun to develop. "Ameliorating," with reference to a disease, pathological condition, or symptom, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, a reduction in the number of relapses of the disease, an improvement in the overall health or well-being of the subject, or by other parameters well known in the art that are specific to the particular disease.

Isolated: An "isolated" or "purified" biological component (such as a nucleic acid, peptide, protein, protein complex, or particle) has been substantially separated, produced apart from, or purified away from other biological components in the cell of the organism in which the component naturally occurs, that is, other chromosomal and extrachromosomal DNA and RNA, and proteins. Nucleic acids, peptides and proteins that have been "isolated" or "purified" thus include nucleic acids and proteins purified by standard purification methods. The term also embraces nucleic acids, peptides and proteins prepared by recombinant expression in a host cell, as well as chemically synthesized nucleic acids or proteins. The term "isolated" or "purified" does not require absolute purity; rather, it is intended as a relative term. Thus, for example, an isolated biological component is one in which the biological component is more enriched than the biological component is in its natural environment within a cell, or other production vessel. Preferably, a preparation is purified such that the biological component represents at least 50%, such as at least 70%, at least 90%, at least 95%, or greater, of the total biological component content of the preparation.

Label: A composition detectable by spectroscopic, photochemical, biochemical, immunochemical, or chemical means. For example, useful labels include $^{32}P$ (or other radioisotopes), fluorescent dyes, fluorescent proteins, electron-dense reagents (for example, colloidal gold or ferritin), enzymes (for example, for use in an ELISA), biotin, digoxigenin, or haptens and proteins or peptides for which antisera or monoclonal antibodies are available. A label often generates a measurable signal, such as radioactivity, fluorescent light or enzyme activity, which can be used to detect and/or quantitate the amount of labeled molecule.

Marinobufagenin (MBG): 3β,5β-dihydroxy-14,15-epoxy bufadienolide (CAS Reg. No. 470-42-8), a bufadienolide originally discovered in amphibians, inhibits $Na^+/K^+$-ATPase activity and cross-reacts with digitalis antibodies (Flier et al., *Science* 208:503-05, 1980). Marinobufagenin may be also referred to as marinobufagin. Marinobufagenin immunoreactive material purified from human and rat urine is identical to MBG from the toad *Bufo marinus*, by mass spectral analysis and by its ability to inhibit rat kidney $Na^+/K^+$-ATPase (Bagrov et al., *Hypertension* 31:1097-1103, 1998; Fedorova et al., *Hypertension* 37:462-66, 2001; and Komiyama et al., *Clin. Biochem.* 38:36-45, 2005).

Monoclonal antibody: An antibody produced by a single clone of B-lymphocytes or by a cell into which the light and heavy chain genes of a single antibody have been transfected. Monoclonal antibodies are produced by methods known to those of skill in the art, for instance by making hybrid antibody-forming cells from a fusion of myeloma cells with immune spleen cells (see, for example, Kohler and Milstein, *Nature* 256:495-97, 1975).

Myocardial Fibrosis The development of fibrous tissue in the heart muscle. In some examples the muscle fibers are replaced with fibrous tissue. "Myocardial fibrosis" is seen and exaggerated interstitial and perivascular accumulation of fibrillar collagens type I and type III is found in the myocardium of patients with arterial hypertension and left ventricular hypertrophy. with increased frequency and severity in patients with systolic and diastolic left ventricular (LV) dysfunction. Myocardial fibrosis is one of the histologic constituents of myocardial remodeling present in hypertensive patients with hypertensive heart disease. Hypertensive myocardial fibrosis facilitates abnormalities of cardiac function, coronary reserve, and electrical activity that adversely affect the clinical outcome of hypertensive patients. In some examples, myocardial fibrosis is induced by pressure overload hypertension or increased levels of angiotensin.

Paratope: That portion of an antibody that is responsible for its binding to an antigenic determinant (epitope) on an antigen.

Pharmaceutically acceptable carriers: The pharmaceutically acceptable carriers useful with compositions described herein are conventional. Martin, *Remington's Pharmaceutical Sciences*, published by Mack Publishing Co., Easton, Pa., 19th Edition, 1995, describes compositions and formulations suitable for pharmaceutical delivery of the mAbs disclosed herein.

In general, the nature of the carrier will depend on the particular mode of administration being employed. For instance, parenteral formulations usually include injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically-neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Polypeptide: A polymer in which the monomers are amino acid residues joined together through amide bonds. When the amino acids are alpha-amino acids, either the L-optical isomer or the D-optical isomer can be used, the L-isomers being preferred for many biological uses. The terms "polypeptide" or "protein" as used herein are intended to encompass any amino acid molecule and include modified amino acid molecules such as glycoproteins. The term "polypeptide" is specifically intended to cover naturally occurring proteins, as well as those which are recombinantly or synthetically produced.

Preeclampsia: A toxemia of late (after the 20th week of gestation) pregnancy, characterized by hypertension, edema and proteinuria. The American College of Obstetrics and Gynecology defines "preeclampsia" as including a diastolic blood pressure of at least 90 mm Hg or a systolic blood pressure of at least 140 mm Hg, or a rise in the former of at least 15 mm Hg or in the latter of 30 mm Hg on at least two occasions 6 hours or more apart, proteinuria (presence of 300 mg or more of protein in a 24-hour urine collection or a protein concentration of 1 g or more per liter in at least two random urine specimens collected 6 hours or more apart) or edema (a generalized accumulation of fluid of greater than 1+ pitting edema after 12 hours of bed rest or weight gain of 5 pounds or more in 1 week), or both, induced by pregnancy after the 20th week of gestation, and sometimes earlier.

Recombinant nucleic acid: A nucleic acid molecule that is not naturally occurring or has a sequence that is made by an artificial combination of two otherwise separated segments of sequence. This artificial combination is accomplished by chemical synthesis or, more commonly, by the artificial manipulation of isolated segments of nucleic acids, for example, by genetic engineering techniques such as those described in Sambrook et al. (ed.), *Molecular Cloning: A Laboratory Manual*, 2$^{nd}$ ed., vol. 1-3, Cold Spring Harbor Laboratory Press, Cold Spring Harbor, N.Y., 1989. The term recombinant includes nucleic acids that have been altered solely by addition, substitution, or deletion of a portion of a natural nucleic acid molecule.

Sample: A portion, piece, or segment that is representative of a whole. This term encompasses any material, including for instance samples obtained from an animal, a plant, or the environment.

A "biological sample" is a sample obtained from a plant or animal subject. As used herein, biological samples include all clinical samples useful for detection of MBG in subjects, including, but not limited to, cells; tissues; bodily fluids, such as blood, derivatives and fractions of blood, such as serum; biopsied or surgically removed tissue, including tissues that are, for example, unfixed, frozen, fixed in formalin and/or embedded in paraffin; skin scrapes; urine; sputum; cerebrospinal fluid; saliva; and cervical swabs. In particular embodiments, the biological sample is obtained from an animal subject, such as blood, serum or urine.

Therapeutically effective amount: The amount of an agent or compound (including an antibody, such as a mAb or an antigen to stimulate production of an antibody) that is sufficient to prevent, treat, reduce, and/or ameliorate the symptoms and/or underlying causes of any disorder or disease. In one embodiment, a "therapeutically effective amount" is sufficient to reduce or eliminate a symptom of a hypertension disorder. In another embodiment, a therapeutically effective amount is an amount sufficient to overcome the disease itself.

A therapeutically effective amount can be endogenously produced (as in an immune response to an antigen) or exogenously administered in a single dose, or in several doses, for example daily, during a course of treatment. However, the effective amount will be dependent on the subject being treated, the severity and type of the condition, and the manner of administration of the agent. "Administering" can be accomplished by introducing the therapeutically effective amount locally or systemically into the subject. Systemic introduction can be accomplished by using an intravenous, intramuscular, transcutaneous or subcutaneous means. Such means could include introducing the therapeutically effective amount via injection, or via catheter. Local administration can be accomplished, for example, by direct injection into the affected area, or by implanting a substrate for controlled release.

The therapeutically effective amount can be produced or administered in all animals (for example, humans, apes, dogs, cats, horses, and cows) that have or may develop a disorder.

Transformed: A "transformed" cell is a cell into which has been introduced a nucleic acid molecule by molecular biology techniques. The term encompasses all techniques by which a nucleic acid molecule might be introduced into such a cell, including transfection with viral vectors, transformation with plasmid vectors, and introduction of naked DNA by electroporation, lipofection, and particle gun acceleration.

Uremic Cardiomyopathy: Subjects with chronic renal failure develop "uremic cardiomyopathy," a disease state characterized by diastolic dysfunction, cardiac, hypertrophy, and systemic oxidant stress.

Vector: A nucleic acid molecule as introduced into a host cell, thereby producing a transformed host cell. A vector may include nucleic acid sequences that permit it to replicate in a host cell, such as an origin of replication. A vector may also include one or more selectable marker genes and other genetic elements known in the art.

As used herein, the singular terms "a," "an," and "the" include plural referents unless context clearly indicates otherwise. Similarly, the word "or" is intended to include "and" unless the context clearly indicates otherwise. Also, as used herein, the term "comprises" means "includes." Hence "comprising A or B" means including A, B, or A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. The materials, methods, and examples are illustrative only and not intended to be limiting.

III. Overview of Several Embodiments

Provided herein are compositions that include hybridoma cell lines. In specific embodiments, these hybridoma cell lines include the hybridoma cell lines having the identifying characteristics of cell lines deposited on May 24, 2005 with the ATCC under ATCC accession number PTA-6724 (3E9 hybridoma) or PTA-6725 (4G4 hybridoma), or the cell line deposited on Jun. 16, 2005 with the ATCC under ATCC accession number PTA-6788 (4H2 hybridoma).

Other embodiments include polyclonal antibodies, mAbs and antigen binding fragments that specifically bind MBG. Specific examples of such mAbs and antigen binding fragments include the mAbs produced by the deposited hybridoma cell lines or hybridoma cell lines having the identifying characteristics of the deposited hybridoma cell lines, and antigen binding fragments thereof. Additional examples include mAbs that are modified by recombinant or other synthetic means and retain the characteristics of mAbs produced by the deposited hybridoma cell lines. In specific embodiments, the mAbs and antigen binding fragments are labeled with a detectable agent, for instance, an electron-dense compound, an enzyme, a fluorochrome, a hapten, or a radioisotope.

Also provided herein is a method of detecting the presence of MBG in a biological sample. This method includes contacting the sample with a mAb produced by the deposited hybridoma cell lines and detecting the binding of the mAb with the sample, thereby detecting MBG in the sample. In a specific, non-limiting example, the mAb is labeled with a detectable agent to detect MBG in the sample. In another specific, non-limiting example, detecting MBG in the sample includes contacting the sample with a second antibody that specifically binds a mAb produced by the deposited hybridoma cell lines.

Additional embodiments include a method of diagnosing cardiovascular disease in a subject. This method involves contacting a biological sample from a subject with a mAb produced by the deposited hybridoma cell lines and detecting the binding of the mAb with the sample, wherein binding of the mAb to the sample is indicative of the diagnosis of cardiovascular disease in the subject. In some examples the method is a method of diagnosing hypertension in a subject. In a specific, non-limiting example, the method is a method of diagnosing essential hypertension, preeclampsia, eclampsia, uremic cardiomyopathy, or myocardial fibrosis. In a further specific, non-limiting example, the mAb is labeled with a detectable agent, and detecting the binding includes detecting the detectable agent.

Yet another embodiment is a method of treating or inhibiting cardiovascular disease, as in a subject with hypertension, such as essential hypertension, hypertension associated preeclampsia, eclampsia, or renal failure, or in a subject with myocardial fibrosis. In one embodiment, a subject is selected who has the cardiovascular disease and the subject is exposed to a therapeutically effective amount of an anti-MBG antibody, or an antigen binding fragment thereof. The anti-MBG antibody can for example be produced by the deposited hybridoma cell lines or hybridoma cell lines having the identifying characteristics of the deposited hybridoma cell lines. The subject may be exposed to the anti-MBG antibody, for example by provoking an antibody response or administering a mAb produced by the deposited hybridoma cell lines in a pharmaceutically acceptable carrier, to treat or inhibit the condition. In non-limiting examples, the method is a method of treating a human subject, for instance, a subject who has essential hypertension, hypertension associated preeclampsia, eclampsia, or uremic cardiomyopathy, or myocardial fibrosis.

In some embodiments, treatment of cardiovascular disease with an anti-MBG antibody can result in the reduction of blood pressure, for example in a subject with essential hypertension, hypertension associated preeclampsia, or renal failure. In some particular embodiments, treatment of hypertension with an anti-MBG antibody can result in a reduction of symptoms associated with hypertension. For example, treatment with an anti-MBG antibody can result in an attenuation of symptoms of uremic cardiomyopathy, such as cardiac hypertrophy, oxidant stress, and cardiac fibrosis, such as myocardial fibrosis. In other embodiments the treatment with an anti-MBG antibody can result in attenuation of cardiac hypertrophy, oxidant stress, and cardiac fibrosis, such as myocardial fibrosis, where no hypertension is present.

Amounts effective for this use will depend upon the severity of the disease and the general state of the patient's health. A therapeutically effective amount of the antibody can provide either subjective relief of a symptom(s) or an objectively identifiable improvement as noted by the clinician or other qualified observer. These compositions can be administered in conjunction with a therapeutically effective amount of an a different anti-hypertensive agent, such as an angiotensin-converting enzyme inhibitor, an angiotensin receptor blocker, a diuretic, a calcium channel blocker, an alpha-adrenoceptor blocker, an endothelin-1 receptor blocker, an organic nitrate, a protein kinase C inhibitor, or a combination thereof. The other agents can be administered either simultaneously or sequentially in sufficient temporal proximity to provide a combined therapeutic effect.

IV. Marinobufagenin

Expansion of plasma volume and/or NaCl loading is known to stimulate the production of endogenous SPLs that promote natriuresis via inhibition of the $Na^+/K^+$-ATPase in renal tubules (Blaustein M P, *Am. J. Physiol.* 264:C1367-87, 1993). Mammalian SPLs include endogenous ouabain, a cardenolide (Blaustein M P, *Am. J. Physiol.* 264:C1367-87, 1993), and MBG, a bufadienolide (Bagrov et al., *Hypertension* 31:1097-1103, 1998). Marinobufagenin (3β,5β-dihydroxy-14,14-epoxybufadienolide), a bufadienolide originally discovered in amphibians, inhibits $Na^+/K^+$-ATPase activity and cross-reacts with digitalis antibodies (Flier et al., *Science* 208:503-05, 1980). Marinobufagenin exhibits high affinity towards the ouabain-resistant α-1 rodent $Na^+/K^+$-ATPase, the main sodium pump isoform in renal tubules and arterial smooth muscle (Fedorova et al., *Am. J. Hypertens.* 10:929-35, 1997 and Fedorova et al., *Hypertension* 37:462-66, 2001). Marinobufagenin is sensitive to plasma volume expansion (Fedorova et al., *Clin. Exp. Hypertens.* 20:581-91, 1998 and Bagrov et al., *Cardiovas. Res.* 206:296-305, 1996) and, in vitro, acts as a vasoconstrictor (Fedorova et al., *Am. J. Hypertens.* 10:929-35, 1997 and Lopatin et al., *J. Hypertens.* 17:1179-87, 1999).

Marinobufagenin (MBG) immunoreactive material purified from human and rat urine is identical to MBG from the toad *Bufo marinus*, by mass spectral analysis and by its ability to inhibit rat kidney $Na^+/K^+$-ATPase (Bagrov et al., *Hypertension* 31:1097-1103, 1998 and Fedorova et al., *Hypertension* 37:462-66, 2001). Marinobufagenin becomes elevated and contributes to hypertension in Dahl-S rats on a chronic high NaCl intake (Fedorova et al., *Circulation* 105:1122-27, 2002), and enhanced MBG production occurs in pathological states associated with fluid retention, including preeclampsia (Lopatin et al., *J. Hypertens.* 17:1179-87, 1999).

Marinobufagenin can be obtained from the crude venom from the parotid glands of the toad *Bufo marinus*. Briefly, liquid venom is obtained by gently pressing on the skin around the glands. The venom crystallizes at room temperature, and the crystallized poison is extracted using ethanol. Following the alcoholic extraction, the mixture is filtered and washed with ethanol. After removal of the filtrate the residue is further extracted with a solution of ethanol and chloroform followed by centrifugation in order to obtain chloroform and ethanol phases. The chloroform phases are isolated and extracted by centrifugation after which the chloroform phases are mixed and distilled under vacuum. The resulting dark brown oily residue is dissolved in ethyl acetate, the non-soluble residue separated by filtration, and the mixture of steroid compounds obtained is separated by thin-layer chromatography.

V. Anti-Marinobufagenin Antibodies

Antibodies which specifically bind to MBG can be prepared using MBG as an antigen. In one embodiment, MBG is conjugated to a carrier protein. Commonly used carrier proteins include, but are not limited to, bovine serum albumin (BSA), keyhole limpet hemocyanin, thyroglobulin, tetanus toxoid, cholera toxoid, ovalbumin, hemolysin, and synthetic peptides. The coupled MBG is used to immunize an appropriate animal (for example, a mouse, a rabbit, or a human). Polyclonal antibodies, antibodies which consist essentially of pooled monoclonal antibodies with different epitopic specificities, as well as distinct monoclonal antibody preparations are encompassed by the present disclosure.

The preparation of polyclonal antibodies is well known to those skilled in the art. See, for example, Green et al., "Production of Polyclonal Antisera," in: *Immunochemical Protocols* pages 1-5, Manson, ed., Humana Press 1992; Coligan, Kruisbeek, Margulies, Shevach, and Strober, Eds. *Current Protocols in Immunology*, John Wiley & Sons Inc. Baltimore, 1997.

The preparation of monoclonal antibodies likewise is conventional. See, for example, Kohler & Milstein, *Nature* 256: 495-97, 1975; Coligan, Kruisbeek, Margulies, Shevach, and Strober, Eds. *Current Protocols in Immunology*, John Wiley & Sons Inc. Baltimore, 1997; and Harlow and Lane, *Using Antibodies: A Laboratory Manual*, CSHL, New York, 1999. Briefly, monoclonal antibodies can be obtained by injecting mice with a composition comprising an antigen of interest (for example, MBG conjugated to a carrier protein), verifying the presence of antibody production by removing a serum sample, removing the spleen to obtain B lymphocytes, fusing the B lymphocytes with myeloma cells to produce hybridomas, cloning the hybridomas, selecting positive clones that produce antibodies to the antigen, and isolating the antibodies from the hybridoma cultures. Monoclonal antibodies can be isolated and purified from hybridoma cultures by a variety of well established techniques. Such isolation techniques include affinity chromatography with Protein-A Sepharose, size-exclusion chromatography and ion-exchange chromatography. See, for example, Coligan, Kruisbeek, Margulies, Shevach, and Strober, Eds. *Current Protocols in Immunology*, John Wiley & Sons Inc. Baltimore, 1997; Barnes et al., "Purification of Immunoglobulin G (IgG)," in: *Methods in Molecular Biology*, Vol. 10, pages 79-104, Humana Press, 1992. Specific, non-limiting examples of monoclonal antibodies include the 3E9, 4G4 and 4H2 mAbs.

Methods of in vitro and in vivo multiplication of hybridomas that produce monoclonal antibodies are well known to those skilled in the art. Multiplication in vitro may be carried out in suitable culture media such as Dulbecco's Modified Eagle Medium or RPMI 1640 medium, optionally supplemented by a mammalian serum such as fetal calf serum, or trace elements and growth-sustaining supplements such as normal mouse peritoneal exudate cells, spleen cells, thymocytes or bone marrow macrophages. Production in vitro provides relatively pure antibody preparations and allows scale-up to yield large amounts of the desired antibodies. Large-scale hybridoma cultivation can be carried out by homogenous suspension culture in an airlift reactor, in a continuous stirrer reactor or in immobilized or entrapped cell culture. Multiplication in vivo may be carried out by injecting cell clones into mammals histocompatible with the parent cells, for example, syngeneic mice, to cause growth of antibody-producing tumors. Optionally, the animals are primed with a hydrocarbon, especially oils such as pristane (tetramethylpentadecane) prior to injection. After one to three weeks, the desired monoclonal antibody is recovered from the body fluid of the animal.

Antibodies can also be derived from a subhuman primate antibody. General techniques for raising therapeutically useful antibodies in baboons can be found, for example, in PCT Publication No. WO 91/11465, 1991 and Losman et al., *Int. J. Cancer* 46:310-14, 1990.

Alternatively, an antibody that specifically binds MBG can be derived from a humanized monoclonal antibody. Humanized monoclonal antibodies are produced by transferring mouse complementarity determining regions from heavy and light variable chains of the mouse immunoglobulin into a human variable domain, and then substituting human residues in the framework regions of the murine counterparts. The use of antibody components derived from humanized monoclonal antibodies obviates potential problems associated with the immunogenicity of murine constant regions. General techniques for cloning murine immunoglobulin variable domains are described, for example, by Orlandi et al., *Proc. Nat'l Acad. Sci. U.S.A.* 86:3833-37, 1989. Techniques for producing humanized monoclonal antibodies are described, for example, by Jones et al., *Nature* 321:522-25, 1986; Riechmann et al., *Nature* 332:323-27, 1988; Verhoeyen et al., *Science* 239:1534-36, 1988; Carter et al., *Proc. Nat'l Acad. Sci. U.S.A.* 89:4285-89, 1992; Sandhu, *Crit. Rev. Biotech.* 12:437-62, 1992; and Singer et al., *J. Immunol.* 150: 2844-57, 1993.

Antibodies can be derived from human antibody fragments isolated from a combinatorial immunoglobulin library. See, for example, Barbas et al., in: *Methods: a Companion to Methods in Enzymology*, Vol. 2, page 119, 1991; Winter et al., *Ann. Rev. Immunol.* 12:433-55, 1994. Cloning and expression vectors that are useful for producing a human immunoglobulin phage library can be obtained, for example, from Stratagene Cloning Systems (La Jolla, Calif.).

In addition, antibodies can be derived from a human monoclonal antibody. Such antibodies are obtained from transgenic mice that have been "engineered" to produce specific human antibodies in response to antigenic challenge. In this technique, elements of the human heavy and light chain loci are introduced into strains of mice derived from embryonic stem cell lines that contain targeted disruptions of the endogenous heavy and light chain loci. The transgenic mice can synthesize human antibodies specific for human antigens, and the mice can be used to produce human antibody-secreting hybridomas. Methods for obtaining human antibodies from transgenic mice are described, for example, by Green et al., *Nature Genet.* 7:13-21, 1994; Lonberg et al., *Nature* 368: 856-59, 1994; and Taylor et al., *Int. Immunol.* 6:579-91, 1994.

Antibodies include intact molecules as well as fragments thereof, such as Fab, F(ab')$_2$, and Fv which are capable of binding the antigenic determinant. These antibody fragments retain some ability to selectively bind with their antigen or receptor and are defined as follows:

(1) Fab, the fragment which contains a monovalent antigen-binding fragment of an antibody molecule, can be produced by digestion of whole antibody with the enzyme papain to yield an intact light chain and a portion of one heavy chain;

(2) Fab', these fragments of an antibody molecule can be obtained by treating whole antibody with pepsin, followed by reduction, to yield an intact light chain and a portion of the heavy chain (including the hinge region); two Fab' fragments are obtained per antibody molecule;

(3) F(ab')$_2$, the fragment of an antibody that can be obtained by treating whole antibody with the enzyme pepsin, without subsequent reduction; F(ab')$_2$ is a dimer of two Fab' fragments held together by two disulfide bonds;

(4) Fv, a genetically engineered fragment containing the variable region of a light chain and the variable region of a heavy chain, expressed as two chains; and (5) SCA, a genetically engineered molecule containing the variable region of a light chain and the variable region of a heavy chain, linked by a suitable polypeptide linker, as a genetically fused single chain molecule.

Methods of making these fragments are known in the art. (See, for example, Harlow and Lane, *Using Antibodies: A Laboratory Manual*, CSHL, New York, 1999). Antibody fragments can be prepared by proteolytic hydrolysis of the antibody or by expression in *E. coli* of DNA encoding the fragments. Antibody fragments can be obtained by pepsin or papain digestion of whole antibodies by conventional methods. For example, antibody fragments can be produced by enzymatic cleavage of antibodies with pepsin to provide a 5S fragment denoted F(ab')$_2$. This fragment can be further cleaved using a thiol reducing agent (and optionally a blocking group for the sulfhydryl groups resulting from cleavage of disulfide linkages), to produce 3.5S Fab' monovalent fragments. Alternatively, an enzymatic cleavage using papain produces two monovalent Fab fragments and an Fc fragment directly (see U.S. Pat. No. 4,036,945 and U.S. Pat. No. 4,331,647, and references contained therein; Nisonhoff et al., *Arch. Biochem. Biophys.* 89:230-44, 1960; Porter, *Biochem. J.* 73:119-26, 1959; Edelman et al., *Methods in Enzymology*, Vol. 1, page 422, Academic Press, 1967; and Coligan, Kruisbeek, Margulies, Shevach, and Strober, Eds. *Current Protocols in Immunology*, John Wiley & Sons Inc. Baltimore, 1997).

Other methods of cleaving antibodies, such as separation of heavy chains to form monovalent light/heavy chain fragments, further cleavage of fragments, or other enzymatic, chemical, or genetic techniques may also be used, so long as the fragments bind to the antigen that is recognized by the intact antibody.

For example, Fv fragments include an association of V$_H$ and V$_L$ chains. This association may be noncovalent (Inbar et al., *Proc. Nat'l Acad. Sci. U.S.A.* 69:2659-62, 1972). Alternatively, the variable chains can be linked by an intermolecular disulfide bond or cross-linked by chemicals such as glutaraldehyde (see, for example, Sandhu, *Crit. Rev. Biotech.* 12:437-62, 1992). The Fv fragments can include V$_H$ and V$_L$ chains connected by a peptide linker. These SCFvs are prepared by constructing a structural gene including DNA sequences encoding the V$_H$ and V$_L$ domains connected by an oligonucleotide. The structural gene is inserted into an expression vector, which is subsequently introduced into a host cell (such as *E. coli*). The recombinant host cell synthesizes a single polypeptide chain with a linker peptide bridging the two V domains. Methods for producing SCFvs are known in the art (see, for example, Whitlow et al., *Methods: a Companion to Methods in Enzymology*, Vol. 2, page 97, 1991; Bird et al., *Science* 242:423-26, 1988; U.S. Pat. No. 4,946,778; Pack et al., *BioTechnology* 11:1271-77, 1993; and Sandhu, *Crit. Rev. Biotech.* 12:437-62, 1992).

Another form of an antibody fragment is a peptide coding for a single CDR. CDR peptides ("minimal recognition units") can be obtained by constructing genes encoding the CDR of an antibody of interest. Such genes are prepared, for example, by using the polymerase chain reaction to synthesize the variable region from RNA of antibody-producing cells (Larrick et al., *Methods: a Companion to Methods in Enzymology*, Vol. 2, page 106, 1991).

Polyclonal or monoclonal antibodies can be purified, for example, by binding to and elution from a matrix to which the antigen to which the antibodies were raised is bound. Those of skill in the art will know of various techniques common in the immunology arts for purification and/or concentration of polyclonal antibodies, as well as monoclonal antibodies (see, for example, Coligan, Kruisbeek, Margulies, Shevach, and Strober, Eds. *Current Protocols in Immunology*, John Wiley & Sons Inc. Baltimore, 1997).

Optimally, antibodies raised against MBG will specifically detect MBG. That is, antibodies raised against MBG will recognize and bind MBG, and will not substantially recognize or bind to other bufadienolides, cardenolides or other steroids. The determination that an antibody specifically binds to a target antigen (that is, binding affinity for a target antigen) is typically measured or determined by standard antibody-antigen assays, such as competitive assays, saturation assays, or any one of a number of standard immunoassay methods; for instance, the Western blotting technique (Sambrook et al. (ed.), *Molecular Cloning: A Laboratory Manual*, $2^{nd}$ ed., vol. 1-3, Cold Spring Harbor Laboratory Press, Cold Spring Harbor, N.Y., 1989), antigen enzyme-linked immunoabsorbent assay (ELISA), radioimmunoassay (RIA), or indirect immuno-fluorescence assay (IFA). Such assays can be used to determine the dissociation constant of the antibody. The phrase "dissociation constant" refers to the affinity of an antibody for an antigen. Specificity of binding between an antibody and an antigen exists if the dissociation constant ($K_D=1/K$, where K is the affinity constant) of the antibody is, for example <1 µM, <100 nM, or <0.1 nM. Antibody molecules will typically have a $K_D$ in the lower ranges. $K_D$=[Ab–Ag]/[Ab][Ag] where [Ab] is the concentration at equilibrium of the antibody, [Ag] is the concentration at equilibrium of the antigen and [Ab–Ag] is the concentration at equilibrium of the antibody-antigen complex. Typically, the binding interactions between antigen and antibody include reversible non-covalent associations such as electrostatic attraction, Van der Waals forces, and hydrogen bonds.

There are many assays known in the art that measure the competition of antibodies for binding to an antigen (see, for example, Wagener et al., *J. Immunol.*, 130:2308-15, 1983; Ransom, *Practical Competitive Binding Assay Methods*, Philadelphia: Elsevier (C. V. Mosby), 1976; Harlow and Lane, *Using Antibodies: A Laboratory Manual*, CSHL, New York, 1999). In one representative competition assay, a first antibody is immobilized to a solid support, such as to one or more wells of a 96-well microplate. A labeled target antigen (for example fluorochrome-labeled) is then applied in a solution that either contains or lacks a soluble second antibody. After sufficient time for antibody-antigen interaction (for example, 30-60 minutes), the unbound target antigen and unbound second antibody are both washed away. Binding of the labeled target antigen by the immobilized first antibody can be determined by measuring the amount of label (for example, fluorescence) bound to the well. If the second antibody binds to the same antigen as the immobilized first antibody, then the second antibody will compete with the first antibody for this antigen, thereby reducing the amount of labeled target antigen bound per well. The amount of such reduction will vary as a function of second antibody concentration.

The monoclonal antibodies of this disclosure can be bound to a substrate (for example, beads, tubes, slides, plates, nitrocellulose sheets, and the like) or conjugated with a detectable moiety, or both bound and conjugated. The detectable moieties contemplated for the present disclosure can include, but are not limited to, an immunofluorescent moiety (for example, fluorescein, rhodamine), a radioactive moiety (for example, $^{32}P$, $^{125}I$, $^{35}S$), an enzyme moiety (for example, horseradish peroxidase, alkaline phosphatase), a colloidal gold moiety, and a biotin moiety. Such conjugation techniques are standard in the art (for example, see Harlow and Lane, *Using Antibodies: A Laboratory Manual*, CSHL, New York, 1999; Yang et al., *Nature,* 382:319-24, 1996). For example, polypeptides typically contain a variety of functional groups, such as carboxylic acid (COOH), free amine (—$NH_2$) or sulfhydryl (—SH) groups, which are available for reaction with a suitable functional group on an antibody to result in the binding of the detectable moiety. Alternatively, the antibody is derivatized to expose or attach additional reactive functional groups. The derivatization may involve attachment of any of a number of linker molecules. The linker can be any molecule used to join the antibody to the detectable moiety. A linker is capable of forming covalent bonds to both the antibody and to the detectable moiety. Suitable linkers are well known to those of skill in the art and include, but are not limited to, straight or branched-chain carbon linkers, heterocyclic carbon linkers or peptide linkers. Where the detectable moiety is a polypeptide, the linker may be joined to the constituent amino acids of the antibody and the polypeptide through their side groups (for example, through a disulfide linkage to cysteine) or to the alpha carbon amino and carboxyl groups of the terminal amino acids.

VI. Methods of Using Anti-Marinobufagenin Antibodies

The 3E9, 4G4 and 4H2 mAbs disclosed herein can be used as experimental research tools, or for diagnostic, prophylactic or therapeutic purposes in a clinical setting. Additionally, these mAbs can be used to detect and/or monitor MBG in a subject.

A. Detection of Marinobufagenin

The 3E9, 4G4 and 4H2 mAbs disclosed herein are useful in diagnostic and prognostic evaluation of diseases and disorders, particularly hypertension associated with enhanced MBG production. At each stage of disease, the mAbs can be used to improve diagnostic accuracy and facilitate treatment decisions.

In some embodiments, the 3E9, 4G4 and 4H2 mAbs are used to detect the presence of MBG within an original or processed sample obtained from a subject. Samples obtained from a subject may include, for example, cells, tissue, blood, serum or urine. The sample in its entirety can be taken solely from the subject, such as by probing or scraping, or can be collected through the addition of some other substance or compound. For example, a sample can simply be blood or urine collected from a subject and aliquotted for contacting with the mAbs. A sample can be analyzed directly, extracted before analysis, or expanded in volume by the addition of a suitable solvent. If the type or volume of sample obtained is not sufficient for screening with the mAbs, the sample can be expanded by the addition of a suitable organic or inorganic solvent.

The sample is contacted with an effective amount of one or more of the 3E9, 4G4 or 4H2 mAbs, and the sample is screened to detect a mAb forming a complex with the MBG, such as detecting the binding reaction between the antibody and the MBG. Detection of an antibody-antigen complex or binding reaction indicates that the sample contains MBG. In some embodiments, the one or more mAbs are labeled with a detectable moiety, such as a fluorescent label, so that its signal changes upon binding to MBG. In other embodiments, MBG in the sample is immobilized on a surface prior to introduction of the labeled mAb, and the amount of the signal, corresponding to the amount of bound labeled mAb, correlates to the amount of MBG in the sample. In still other embodiments, MBG is captured by an immobilized unlabeled first mAb, after which a labeled second mAb is introduced to bind to the captured MBG and produce a signal in proportion to the amount of captured MBG.

The disclosed mAbs can be used in a variety of immunometric assays, including radiolabeled, enzyme, fluorescence, precipitation, agglutination, coagulation, Western blot, grid blot, tissue blot, dot blot, chemiluminescence, light-scattering, electrochemical, dip-stick, or biosensor assays. See, for example, *Principles and Practice of Immunoassays*, Price, C. P. and Newman, D. J. (Eds.), Stockton Press, 1997; *The Immunoassay Handbook; $2^{nd}$ Edition,* Wild, D. (Ed.), Nature Publishing Group, London, 2001. In general, an antibody can be used as a labeled primary reagent in a direct assay or as an unlabeled reagent to be detected by a secondary developing antibody conjugate, such as labeled anti-mouse antibody, in an indirect assay. Additionally, an antibody can be used in a competition assay to detect an antigen or antibody in a sample. For example, antigen in a sample extract can be captured by an unlabeled antibody immobilized on the surface of an ELISA well and then detected by a labeled antibody of the same or different kind and/or specificity. Alternatively, the sample can be suspended in a buffer and mixed directly with an antibody, thus allowing the antibody to form an immune complex with its antigen. The reduction of free antibody due to complex formation can then be determined in a second step, based on solid-phase ELISA with purified antigen, by comparing the relative reactivity of free residual antibody left over after sample incubation (sample reactivity) to that of the same antibody when not mixed with the sample (reference reactivity). The ratio of sample to reference antibody reactivity will be inversely proportional to the amount of antigen in the sample.

The anti-MBG mAbs disclosed herein can also be used to test the effectiveness of an agent in complexing with MBG. In some embodiments, a mAb is mixed with MBG and an agent. The MBG can be from an original or processed sample obtained from a subject, or purified apart from the sample. The mixing of the mAb, MBG, and agent can be accomplished in vitro or in vivo. An agent that complexes with the MBG will inhibit the antibody-MBG binding reaction. Therefore, a decrease in antibody-MBG binding in the presence of the agent compared to some reference standard (for example, background fluorescence) or control (for example, antibody-MBG binding in the absence of the agent) indicates that the agent may interact with the MBG. One exemplary method of assessing antibody-MBG binding is to analyze the kinetics of the binding reaction and determine a rate of binding. Other exemplary methods include determining the total amount of antibody-MBG binding at equilibrium.

B. Pharmaceutical Preparations and Therapy

In addition to detecting the presence of MBG, the 3E9, 4G4 and 4H2 mAbs of the present disclosure can also be used to evaluate the treatment efficacy of a therapeutic approach, such as a method of treating hypertension. The mAbs are utilized to detect the level of MBG before and after certain treatment. Reduction in MBG levels is believed to be an indicator of the effectiveness of the treatment.

In one embodiment, a method is provided for restoring $Na^+/K^+$-ATPase activity in a subject, or for lowering arterial blood pressure in a subject, including administering a therapeutically effective amount of one or more of the 3E9, 4G4 or 4H2 mAbs that alters the level of a MBG, and a pharmaceutically acceptable carrier. Administering the pharmaceutical composition can be accomplished by any means known to one of skill in the art.

A therapeutically effective amount of a mAb of the disclosure can be determined by one skilled in the art and will depend on such factors as the age, body weight, sex and medical condition of the subject, and the particular route of administration of the mAb. The mAb may be administered to a subject intravenously as a bolus or by continuous infusion over a period of time, or by intramuscular, subcutaneous, or intraperitoneal routes. Oral, topical, inhalation routes, or other delivery means known to those skilled in the art are also included in the present disclosure.

Compositions are provided that include one or more of the antibodies that specifically bind MBG are disclosed herein in a carrier. The compositions can be prepared in unit dosage forms for administration to a subject. The amount and timing of administration are at the discretion of the treating physician to achieve the desired purposes. In one example, the antibody that specifically binds MBG is formulated for parenteral administration, such as intravenous administration. Any of the antibodies disclosed herein, variants thereof and humanized forms thereof can be used in these methods.

The compositions for administration can include a solution of the antibody that specifically binds MBG dissolved in a pharmaceutically acceptable carrier, such as an aqueous carrier. A variety of aqueous carriers can be used, for example, water for injection, or water buffered with phosphate, citrate, acetate, and the like to a pH typically of 5.0 to 8.0 (such as 6.0 to 7.0), and/or containing salts, such as sodium chloride, potassium chloride and the like to make isotonic. The carrier can also contain excipients, such as human serum albumin, polysorbate 80, sugars, and amino acids to protect the active mAb. These solutions are sterile and generally free of undesirable matter. These compositions may be sterilized by conventional, well known sterilization techniques. The compositions may contain pharmaceutically acceptable auxiliary substances as required to approximate physiological conditions such as pH adjusting and buffering agents, toxicity adjusting agents and the like, for example, sodium acetate, sodium chloride, potassium chloride, calcium chloride, sodium lactate and the like. The concentration of antibody in these formulations can vary widely, and will be selected primarily based on fluid volumes, viscosities, body weight and the like in accordance with the particular mode of administration selected and the subject's needs.

The concentration of a mAb in these pharmaceutical compositions varies widely, from about 0.1 to 100 mg/ml. A typical pharmaceutical composition for intravenous administration includes about 0.1 to 10 mg of antibody per subject per day. The formulated mAbs are particularly suitable for parenteral administration, and can be administered as an intravenous infusion or by subcutaneous, intramuscular or intravenous injection. Actual methods for preparing parentally administrable pharmaceutical compositions are known to those skilled in the art and are described in more detail in, for example, *Remington's Pharmaceutical Sciences*, published by Mack Publishing Co., Easton, Pa., 19th Edition, 1995.

Antibodies may be provided in lyophilized form and rehydrated with sterile water before administration, although they are also provided in sterile solutions of known concentration. The antibody solution is then added to an infusion bag containing 0.9% Sodium Chloride, USP, and typically administered at a dosage of from 0.5 to 15 mg/kg of body weight. Considerable experience is available in the art in the administration of antibody drugs, which have been marketed in the U.S. since the approval of Rituxan® in 1997. Antibody drugs can be administered by slow infusion, rather than in an intravenous push or bolus. In one example, a higher loading dose is administered, with subsequent, maintenance doses being administered at a lower level. For example, an initial loading dose of 4 mg/kg may be infused over a period of some 90 minutes, followed by weekly maintenance doses for 4-8 weeks of 2 mg/kg infused over a 30 minute period if the previous dose was well tolerated.

Single or multiple administrations of the compositions are administered depending on the dosage and frequency as required and tolerated by the patient. The composition should provide a sufficient quantity of at least one of the antibodies disclosed herein to effectively treat the patient. The dosage can be administered once but may be applied periodically until either, a therapeutic result is achieved, or until side effects warrant discontinuation of therapy. Generally, the dose is sufficient to treat or ameliorate symptoms or signs of disease without producing unacceptable toxicity to the patient.

Controlled release parenteral formulations can be made as implants, oily injections, or as particulate systems. For a broad overview of protein delivery systems see, Banga, A. J., *Therapeutic Peptides and Proteins: Formulation, Processing, and Delivery Systems*, Technomic Publishing Company, Inc., Lancaster, Pa., (1995) incorporated herein by reference. Particulate systems include microspheres, microparticles, microcapsules, nanocapsules, nanospheres, and nanoparticles. Microcapsules contain the therapeutic protein, such as a cytotoxin or a drug, as a central core. In microspheres the therapeutic is dispersed throughout the particle. Particles, microspheres, and microcapsules smaller than about 1 μm are generally referred to as nanoparticles, nanospheres, and nanocapsules, respectively. Capillaries have a diameter of approximately 5 μm so that only nanoparticles are administered intravenously. Microparticles are typically around 100 μm in diameter and are administered subcutaneously or intramuscularly. See, for example., Kreuter, J., *Colloidal Drug Delivery Systems*, J. Kreuter, ed., Marcel Dekker, Inc., New York, N.Y., pp. 219-342 (1994); and Tice & Tabibi, *Treatise on Controlled Drug Delivery*, A. Kydonieus, ed., Marcel Dekker, Inc. New York, N.Y., pp. 315-339, (1992) both of which are incorporated herein by reference.

Polymers can be used for ion-controlled release of the antibody compositions disclosed herein. Various degradable and nondegradable polymeric matrices for use in controlled drug delivery are known in the art (Langer, *Accounts Chem. Res.* 26:537-542, 1993). For example, the block copolymer, polaxamer 407, exists as a viscous yet mobile liquid at low temperatures but forms a semisolid gel at body temperature. It has been shown to be an effective vehicle for formulation and sustained delivery of recombinant interleukin-2 and urease (Johnston et al., *Pharm. Res.* 9:425-434, 1992; and Pec et al., *J. Parent. Sci. Tech.* 44(2):58-65, 1990). Alternatively, hydroxyapatite has been used as a microcarrier for controlled release of proteins (Ijntema et al., *Int. J. Pharm.* 112:215-224, 1994). In yet another aspect, liposomes are used for controlled release as well as drug targeting of the lipid-capsulated drug (Betageri et al., *Liposome Drug Delivery Systems*, Technomic Publishing Co., Inc., Lancaster, Pa. (1993)). Numerous additional systems for controlled delivery of therapeutic proteins are known (see U.S. Pat. No. 5,055,303; U.S. Pat. No. 5,188,837; U.S. Pat. No. 4,235,871; U.S. Pat. No. 4,501, 728; U.S. Pat. No. 4,837,028; U.S. Pat. No. 4,957,735; U.S. Pat. No. 5,019,369; U.S. Pat. No. 5,055,303; U.S. Pat. No. 5,514,670; U.S. Pat. No. 5,413,797; U.S. Pat. No. 5,268,164; U.S. Pat. No. 5,004,697; U.S. Pat. No. 4,902,505; U.S. Pat.

No. 5,506,206; U.S. Pat. No. 5,271,961; U.S. Pat. No. 5,254,342 and U.S. Pat. No. 5,534,496).

The pharmaceutical compositions can be administered for prophylactic and/or therapeutic treatments, such as to treat hypertension in a subject. In some embodiments the pharmaceutical compositions are used to treat a cardiovascular disease, such as hypertension, preeclampsia, eclampsia, uremic cardiomyopathy or myocardial fibrosis. An amount adequate to accomplish the desired effect is defined as a "pharmaceutically effective amount." Amounts effective for this use will, of course, depend on the severity of the disease and the weight and general state of the subject. Typically, dosages used in vitro can provide useful guidance in the amounts useful for in vivo administration of the pharmaceutical composition, and animal models can be used to determine effective dosages for treatment of particular disorders. Various considerations are described, for example, in Gilman et al., eds., *Goodman And Gilman's: The Pharmacological Bases of Therapeutics*, 8th ed., Pergamon Press, 1990; and *Remington's Pharmaceutical Sciences*, published by Mack Publishing Co., Easton, Pa., 19th Edition, 1995.

The mAbs disclosed herein can be delivered to a subject by single or multiple administrations. Doses of the pharmaceutical compositions for treatment of hypertension will typically contain from 0.01 to 100 mg per kilogram body weight of one or more of the mAbs of the present disclosure, such as from 0.1 to 1 mg, or 1, 2 or 5 to 20 mg per kilogram body weight or as a unit dose, in an amount sufficient to ameliorate the hypertension without causing unacceptable side effects ("pharmaceutically effective dose"). The pharmaceutical composition may be administered once or multiple times, for example, one, two or three times per day, week or month for one to several days, weeks, months or years, or chronically, depending upon the nature and severity of the disease.

For the purpose of treatment of disease, such as the treatment of hypertension, the appropriate dosage of the pharmaceutical compositions will depend on the severity and course of disease, the subject's clinical history and response, the toxicity of the mAbs, and the discretion of the treating physician. The pharmaceutical compositions are suitably administered to the subject at one time or over a series of treatments. The initial candidate dosage may be administered to a subject. The proper dosage and treatment regimen can then be established by monitoring the progress of therapy using conventional techniques known to those of skill in the art. Additionally, the mAbs of the present disclosure can be administered together with one or more additional therapeutic agents, such as are known to those of skill in the art. Other therapies that may be used in conjunction with treatment with the mAbs include the administration a different cardiovascular drug, such as an anti-hypertensive agent, for example, an angiotensin-converting enzyme inhibitor, an angiotensin receptor blocker, a diuretic, a calcium channel blocker, an alpha-adrenoceptor blocker, an endothelin-1 receptor blocker, an organic nitrate, a protein kinase C inhibitor, or a combination thereof. Thus, the treatment regimes of the present disclosure are formulated in a manner allowing the 3E9, 4G4 and 4H2 mAbs to be administered serially, or in combination with one or more additional agents for the treatment of disease, such as hypertension.

MBG can be administered to a subject in order to generate an anti-marinobufagenin antibody. In one embodiment, MBG is conjugated to a carrier protein. Commonly used carrier proteins include, but are not limited to, bovine serum albumin (BSA), keyhole limpet hemocyanin, thyroglobulin, tetanus toxoid, cholera toxoid, ovalbumin, hemolysin, and synthetic peptides. In some examples, MBG, MBG conjugate, or immunogenic fragment thereof provokes production of antibodies that specifically bind to the epitopes recognized by the 3E9, 4G4 and 4H2 mAbs. The MBG, MBG conjugate, or an immunogenic fragment thereof can be administered by any means known to one of skill in the art (see Banga, A., Parenteral Controlled Delivery of Therapeutic Peptides and Proteins, in *Therapeutic Peptides and Proteins*, Technomic Publishing Co., Inc., Lancaster, Pa., 1995) such as by intramuscular, subcutaneous, or intravenous injection, but even oral, nasal, or anal administration is contemplated. In one embodiment, administration is by subcutaneous or intramuscular injection. To extend the time during which the peptide or protein is available to stimulate a response, the peptide or protein can be provided as an implant, an oily injection, or as a particulate system. The particulate system can be a microparticle, a microcapsule, a microsphere, a nanocapsule, or similar particle (see, for example, Banja, supra). A particulate carrier based on a synthetic polymer has been shown to act as an adjuvant to enhance the immune response, in addition to providing a controlled release.

A pharmaceutical composition including MBG or MBG conjugate can be utilized to evoke an anti-marinobufagenin antibody. In one embodiment, MBG, MBG conjugate, or immunogenic ergent, a micelle-forming agent, and an oil. Suitable stabilizing detergents, micelle-forming agents, and oils are detailed in U.S. Pat. Nos. 5,585,103; 5,709,860; 5,270,202; and 5,695,770, all of which are incorporated by reference. A stabilizing detergent is any detergent that allows the components of the emulsion to remain as a stable emulsion. Such detergents include polysorbate, 80 (TWEEN) (Sorbitan-mono-9-octadecenoate-poly(oxy-1,2-ethanediyl; manufactured by ICI Americas, Wilmington, Del.), TWEEN 40™, TWEEN 20™, TWEEN 60™, Zwittergent™ 3-12, TEEPOL HB7™, and SPAN 85™. These detergents are usually provided in an amount of approximately 0.05 to 0.5%, preferably at about 0.2%. A micelle forming agent is an agent which is able to stabilize the emulsion formed with the other components such that a micelle-like structure is formed. Examples of such agents include polymer surfactants described by BASF Wyandotte publications, e.g., Schmolka, *J. Am. Oil. Chem. Soc.* 54:110 (1977), and Hunter et al., *J. Immunol.* 129:1244 (1981), PLURONIC™ L62LF, L101, and L64, PEG1000, and TETRONIC™ 1501, 150R1, 701, 901, 1301, and 130R1. The chemical structures of such agents are well known in the art. In one embodiment, the agent is chosen to have a hydrophile-lipophile balance (HLB) of between 0 and 2, as defined by Hunter and Bennett, *J. Immun.* 133:3167 (1984). The agent can be provided in an effective amount, for example between 0.5 and 10%, most preferably in an amount between 1.25 and 5%.

The oil included in the composition is chosen to promote the retention of the antigen in oil-in-water emulsion, i.e., to provide a vehicle for the desired antigen, and preferably has a melting temperature of less than 65° C. such that emulsion is formed either at room temperature (about 20° C. to 25° C.), or once the temperature of the emulsion is brought down to room temperature. Examples of such oils include squalene, Squalane, EICOSANE™, tetratetracontane, glycerol, and peanut oil or other vegetable oils. In one specific, non-limiting example, the oil is provided in an amount between 1 and 10%, most preferably between 2.5 and 5%. The oil should be both biodegradable and biocompatible so that the body can break down the oil over time, and so that no adverse effects, such as granulomas, are evident upon use of the oil.

An adjuvant can be included in the composition. In one embodiment, the adjuvant is a mixture of stabilizing detergents, micelle-forming agent, and oil available under the name Provax® (IDEC Pharmaceuticals, San Diego, Calif.).

The subject matter of the present disclosure is further illustrated by the following non-limiting Examples.

EXAMPLES

Example 1

Purification and Characterization of Marinobufagenin

This example demonstrates the purification and characterization of MBG from the venom secreted by the parotid glands of the toad *Bufo marinus*.

*Bufo marinus* toad poison was obtained from venom secreted by the parotid glands of *Bufo marinus* male and female adult toads obtained from Wm. A. Lemberger Inc. (Oshkosh, Wis.). The venom was extracted by gently pressing on the skin around the glands. The venom crystallizes at room temperature within 24 hours. Eight hundred milligrams of the crystallized poison was extracted using 50% ethanol at a temperature of 30° C. over a two-week period.

Following the alcoholic extraction, the mixture was filtered through Shott Nr 4 filters. The filtrand was divided into two portions, and each portion was washed with 3 ml 30% ethanol. After removal of the filtrate the residue was further extracted with a 1:1 solution of 50% ethanol and chloroform followed by centrifugation in order to obtain chloroform and ethanol phases. The chloroform phases were isolated and extracted by centrifugation repeated two times after which the chloroform phases were mixed and distilled under vacuum. A dark brown oily residue resulted which was dissolved in 1 ml of ethyl acetate. The non-soluble residue was separated by filtration.

A mixture of steroid compounds was obtained and separated by thin-layer chromatography (Silufol VV 254, Sigma Chemicals; plates were pre-exposed to one hour preincubation at 100° C. and ethyl acetate was used as the eluent). A spot corresponding to MBG was scraped, divided into three portions and extracted with ethyl acetate. HPLC was used to confirm the purity of the MBG (and other steroid compounds) and, where necessary, was used to further purify MBG and the other steroids. The other steroid compounds and substances were scraped from the Silufol plates and treated by the same procedure as the marinobufagenin.

Identification of the individual steroids was performed by visualization under ultraviolet (UV) light (with comparison of chromatographic mobility), spraying a saturated chloroform solution of $SbCl_3$ for color reactions, and UV absorbance characteristics that are typical for marinobufagenin (=300 nM, E=18600). The other steroid compounds included resibufagenin, substance L, bufalin, telocinobufagenin, argentinogenin, gellerbrigenin, jamaicogenin, gellerbrigenol, gamabufotalin, and substance D.

Example 2

Conjugation of Marinobufagenin to a Carrier Protein

This example demonstrates the conjugation of MBG to a carrier protein prior to the generation of anti-MBG mAbs.

Fifty milligrams of purified marinobufagenin was dissolved in 10 ml of absolute dry benzene, followed by the addition of 80 mg of $Ag_2CO_3$. The solution was then heated to boiling, and, while stirring, a solution of 180 mg of acetobromo-D-glucose in 15 ml of dry benzene was added by drops to the marinobufagenin solution. The reaction was controlled by thin-layer chromatography on silica gel; disappearance of the spot corresponding to marinobufagenin showing that conjugation of marinobufagenin with glucose was successful. After the reaction was complete the silver salt was filtered and the filtrand was evaporated. The compound was dissolved in ether, the nondissolvable residue was filtered and the glycoside was crystallized from the filtrand.

Conjugation of marinobufagenin-glycoside with BSA was performed as described by Curd et al. (*Proc. Nat. Acad. Sci.* 68:2401-06, 1971), with minor modifications. Briefly, silver carbonate (320 mg) is added to a suspension of MBG (200 mg) in dry benzene (70 ml). The mixture is heated to reflux and a solution of acetobromo-α-D-glucose (260 mg) in dry benzene (30 ml) is added by drops for 40 minutes. The resulting suspension is heated under reflux for 4 hours, cooled to room temperature and filtered. The filtrate is evaporated in vacuo. The residue is treated by the methanolic solution (1 ml) of sodium methoxide (obtained from 270 mg sodium and 25 ml absolute methanol) for 2 hours at room temperature and evaporated in vacuo. The residue is dissolved in water (2 ml) and acetone (1 ml) and sodium m-periodate (200 mg) is added. The mixture is stirred for 4 hours, $Na_2HPO_4$ (150 mg) is added, then i-erythritol (25 mg) is added and stirred 12 hours to quench the reaction. Acetone is evaporated in vacuo, the residue is dissolved in water (4 ml) and mixed with a solution of BSA (90 mg) in water (3 ml) or porcine thyroglobulin (140 mg) in water (7 ml). After 45 minutes, sodium cyanoborohydride (20 mg) is added, and after 1 hour once more sodium cyanoborohydride (30 mg) is added. The mixture is stirred for 12 hours and dialyzed 2 days against cold water.

Prior to immunization, the conjugate MBG-glycoside-BSA was compared with MBG for its ability to react with polyclonal antidigoxin rabbit antibody, using a DELFIA immunoassay. Equimolar concentrations of MBG and its conjugate demonstrated exactly similar displacement of digoxin standards, therefore, the conjugation procedure did not alter the immunoreactive properties of the MBG.

Example 3

Generation of Hybridomas Secreting Monoclonal Antibodies to Marinobufagenin This example demonstrates the generation of hybridomas that secrete anti-MBG mAbs.

Approximately 1-5 mg/ml of MBG-BSA conjugate in saline solution was emulsified with Freund's complete adjuvant 1:1. Emulsification was carried out by repeatedly squirting the suspension through the nozzle of a syringe. A total dosage of about 0.3 ml of the conjugate/adjuvant mixture was injected into multiple sites in mice (for example, the legs and at the base of the tail). Injections were repeated at intervals of three to five weeks. Approximately ten days after each treatment, a drop of blood was taken from the tail of each mouse and tested for the presence of specific anti-MBG antibodies. Animals yielding the best antiserum were selected for fusion.

After a rest period of one month, 0.2-0.4 ml of the MBG-BSA conjugate solution, without Freund's adjuvant, was injected intravenously into each mouse. Injected mice were sacrificed three to four days later and their spleens removed under sterile conditions. The spleens were placed into a petri dish containing about 5 ml of ice cold 2.5% FCS-DMM and washed gently, then transferred to round-bottomed tubes (cutting them into three or four pieces per spleen), with about 5 ml of fresh 2.5% FCS-DMM. Using a Teflon pestle, the pieces were crushed gently to make cell suspensions. The clumps and pieces of connective tissues were allowed to settle, then the cell suspensions were transferred to round-bottomed tubes. The tubes were filled with 2.5% FCS-DMM and spun at room temperature for 7-10 minutes at 400×g. Pellets were resuspended in about 10 ml of fresh medium and centrifuged as above, then resuspended in 10 ml of medium and the cells counted.

About $10^8$ spleen cells and about $10^7$ myeloma cells (from a culture in logarithmic growth) were mixed together and DMM added to a total volume of 50 ml. The cells were spun down at room temperature for 8 minutes at about 400×g, the supernatant completely removed with a Pasteur pipette connected to a vacuum line and the pellet dislodged by gently tapping the bottom of the tube. The tube was then placed in a 200-ml beaker containing water at 40° C. and maintained at this temperature during the cell fusion process.

To mediate cell fusion, 0.8 ml of 50% polyethylene glycol (PEG) prewarmed to 40° C. was added to the pellet using a 1-ml pipette, over a period of 1 minute, with continuous stirring of the cells with the pipette tip. Stirring of the cells in 50% PEG was continued for a further 1.5 minutes. One milliliter of 37° C. DMM was then added to the fusion mixture, with continuous stirring as before, over a period of 1 minute. This step was repeated, and then repeated two additional times adding the medium in 30 seconds. With continuous stirring, 6 ml of DMM was then added over a period of about 2 minutes. Twelve to thirteen milliliters of prewarmed DMM (37° C.) was added and the mixture spun down for about 8 minutes at 400×g. The supernatant was discarded and the pellet gently broken up by tapping the bottom of the tube, and then resuspended in approximately 49 ml of 20% FCS-DMM.

The fusion suspension was distributed in the 48 wells of two Linbro plates, with an additional 1 ml of 20% FCS-DMM containing $10^8$ spleen cells/ml added to each well. Plates were incubated overnight at 37° C. in a $CO_2$ incubator. Using a Pasteur pipette connected to a vacuum line, 1 ml of the culture medium was removed from each well without disturbing the cells. Cells were fed with 1 ml of HAT medium/well for 2-3 days, until a vigorous growth of hybrids was evident under the microscope. As the culture became more yellow, it was tested for antibody activity. Duplicates of the growing hybrid cultures were prepared and fed for a week with HAT medium.

Example 4

Cross-Reactivity of the Anti-Marinobufagenin Monoclonal Antibodies

This example demonstrates the specificity (as shown by cross-reactivity) of the 3E9, 4G4 and 4H2 mAbs for marinobufagenin.

The percent cross-reactivity of the 3E9, 4G4 and 4H2 mAbs was defined as the ratio of the amount of MBG required to displace 50% of maximally bound MBG from the particular anti-MBG mAb, versus the amount of the cross-reactant to give the same 50% displacement. The binding specificities of the 3E9 mAb for a panel of steroids are shown in Table I; those for the 4112 and 4G4 mAbs are shown in Table II.

TABLE I

Cross-reactivity of the 3E9 mAb

|  | Cross-reactant | Percent cross-immunoreactivity |
|---|---|---|
| Bufadienolides | MBG | 100 |
|  | Bufalin | 0.25 |
|  | Cinobufagin | 1.4 |
|  | Cinobufotalin | 4 |
|  | Marinobufotoxin | 4 |
|  | Telocinobufotoxin | 7 |
|  | Proscillaridin | 3 |
| Cardenolides | Ouabain | 0.3 |
|  | Digoxin | 1.8 |
|  | Ouabagenin | <0.01 |
|  | Digoxigenin | 1 |
|  | Digitoxin | 0.7 |
| Other steroids | Progesterone | 0.3 |
|  | Spironolactone | 0.22 |
|  | Prednisone | <0.01 |
|  | Corticosterone | <0.01 |

TABLE II

Cross-reactivity of the 4H2 and 4G4 mAbs

| Cross-reactant | 4H2 Percent cross-immunoreactivity | 4G4 Percent cross-immunoreactivity |
|---|---|---|
| MBG | 100 | 100 |
| Bufalin | 0.07 | 0.08 |
| Cinobufagin | 0.11 | 0.07 |
| Cinobufotalin | 58 | 43 |
| Marinobufotoxin | 55 | 44 |
| Ouabain | 0.03 | 0.004 |
| Digoxin | 0.03 | 0.003 |
| Resibufagenin | 0.2 | 0.6 |

Example 5

Effects of the 3E9, 4G4 and 4H2 mAbs on Erythrocyte $Na^+/K^+$-ATPase Activity

This example demonstrates the in vitro effects of the 3E9, 4G4 and 4H2 mAbs on human erythrocyte $Na^+/K^+$-ATPase activity.

Activity of the $Na^+/K^+$-ATPase was measured in erythrocytes obtained from normotensive pregnant women (N pregnant) and from pregnant women with preeclampsia (PE). In one experiment, erythrocytes were obtained from twelve N pregnant women and from nine PE women. In another experiment, erythrocytes were obtained from eight N pregnant women (gestational age=37.5±0.2 weeks) and from ten PE women (gestation age=35.7±1.9 weeks; systolic blood pressure=151±8 mm Hg, diastolic blood pressure=98±5 mm Hg).

In women with preeclampsia, aliquots of whole blood (1.0 ml) were preincubated at room temperature for 30 minutes in the presence of DIGIBIND (1.0 µg/ml) or the 3E9 (0.42 µg/ml), 4G4 (0.25 µg/ml) or 4H2 (0.1 µg/ml) mAbs; this dilution corresponds to the concentration of anti-MBG antibodies, which, in vitro, blocks the $IC_{75}$ of MBG-induced inhibition of $Na^+/K^+$-ATPase from the outer medulla of rat kidney. Erythrocytes were washed three times in an isotonic medium (145 mM NaCl in 20 mM Tris buffer; pH 7.6 at 4° C.). Activity of $Na^+/K^+$-ATPase was determined, as reported in Bagrov et al. (*Hypertension* 26:781-788, 1995). Briefly, erythrocytes were preincubated with Tween-20 (0.5%) in sucrose (250 mM) and Tris buffer (20 mM; pH 7.4, 37° C.) for 30 minutes, and were incubated for 30 minutes in medium containing (in mM): NaCl 100, KCl 10, $MgCl_2$ 3, EDTA 0.5, Tris 50, ATP 2 (pH 7.4, 37° C.) in the final dilution 1:40. The reaction was stopped by the addition of trichloracetic acid to a final concentration of 7%. Total ATPase activity was measured by the production of inorganic phosphate ($P_i$), and $Na^+/K^+$ATPase activity was estimated as the difference between ATPase activity in the presence and in the absence of 1 mmol/L ouabain. Absolute values for erythrocyte $Na^+/K^+$-ATPase activity are shown in Table III; all three mAbs were more effective versus DIGIBIND in restoring $Na^+/K^+$-ATPase activity.

TABLE III

Absolute values for erythrocyte $Na^+/K^+$-ATPase activity

| N pregnant | PE | DIGIBIND | 3E9 | 4H2 | 4G4 |
|---|---|---|---|---|---|
| 2.41 ± 0.22 | 1.54 ± 0.11# | 1.85 ± 0.15 | 2.02 ± 0.06* | 2.05 ± 0.16* | 2.31 ± 0.19* |

(†): $P < 0.01$ vs. N pregnant subjects.
(‡): $P < 0.01$ vs. subjects with PE.
Repeated measures ANOVA followed by Newman-Keul's test.
$P < 0.01$ vs. N pregnant subjects; two-tailed t-test.
*$P < 0.01$ vs. subjects with PE.
Repeated measures ANOVA followed by Dunnett's multiple comparison test.

Example 6

Effect of the 3E9, 4G4 and 4H2 mAbs on Blood Pressure

This example demonstrates the in vivo effect of the 3E9, 4G4 and 4H2 mAbs on blood pressure in rats with hypertension. This laboratory model is often used as an animal model of essential hypertension.

Six week old male Dahl salt-sensitive rats (DS; 245-265 grams, Charles River, Wilmington, Mass.) were fed a high (8%) sodium (HS) chloride (Halan Teklad, Madison, Wis.) diet and water ad libitum. After 3 weeks of HS intake, systolic blood pressure (SBP; mm Hg, measured by tail-cuff plethysmography) was measured before and 90 minutes after acute intraperitoneal administration of a polyclonal anti-MBG antibody and the 3E9 mAb (0.34 mg/kg). The results are shown in Table IV; the 3E9 mAb reduced the SBP in DS rats with experimental salt-sensitive hypertension.

TABLE IV

SBP in hypertensive Dahl rats

| Polyclonal anti-MBG SBP antibody before & after | 3E9 SBP before & after | Nonimmune rabbit serum SBP before & after |
|---|---|---|
| 175 ± 3  128 ± 3† | 189 ± 3  134 ± 4† | 173 ± 5  167 ± 4 |

N = 5-6 per group.
†$P < 0.01$ vs. baseline SBP, one-way ANOVA followed by Bonferroni's test.

A subsequent study was performed on female Sprague-Dawley rats (225-250 grams) purchased from Charles River (Wilmington, Mass.) on day 5 of pregnancy and on nonpregnant, age-matched controls. All animals were housed under controlled diurnal light (6 AM-6 PM) and temperature (21±3° C.). They were fed a normal diet containing 0.7% sodium chloride (Halan Teklad, Madison, Wis.). Control animals (10 pregnant and 10 non-pregnant) received tap water throughout the experiment. The experimental group (pregnant, n=26) drank 1.8% sodium chloride solution beginning on day 12 of gestation. Systolic blood pressure was measured by tail-cuff plethysmography. 24-hr water consumption was monitored, and 24-hour urine samples were collected at days 7, 11, 15, and 19 of pregnancy, or at corresponding times in the control group. Aliquots of urine (0.5 ml) were extracted on C18 reverse-phase columns to measure the concentrations of MBG.

The effect of DIGIBIND, a polyclonal anti-MBG antibody and the 3E9, 4G4 and 4H2 mAbs on SBP was compared in a subset of pregnant rats following NaCl supplementation for 7 days. Preimmune rabbit serum (n=7), polyclonal anti-MBG antibody (n=7) or the 3E9, 4G4 and 4H2 mAbs (n=7) were administered intraperitoneally at a concentration which in vitro reverses MBG-induced inhibition of rat kidney $Na^+/K^+$-ATPase. Following antibody administration, SBP was measured hourly for three hours. The results are shown in FIG. 1; administration of the 3E9, 4G4 and 4H2 mAbs reduced the SBP.

Example 7

Effect of the 3E9 mAb on $Na^+/K^+$-ATPase Activity in the Thoracic Aorta

This example demonstrates the in vitro effect of the 3E9 mAb on $Na^+/K^+$-ATPase activity in the thoracic aorta of rats with pregnancy-associated hypertension.

Female Sprague-Dawley rats (225-250 grams) were purchased from Charles River (Wilmington, Mass.). Day 5 pregnant and on nonpregnant, age-matched controls were used in this study. All animals were housed under controlled diurnal light (6 AM-6 PM) and temperature (21±3° C.). They were fed a normal diet containing 0.7% sodium chloride (Halan Teklad, Madison, Wis.). Control animals (10 pregnant and 10 non-pregnant) received tap water throughout the experiment. The experimental group (pregnant, n=26) drank 1.8% sodium chloride solution beginning on day 12 of gestation. Systolic blood pressure was measured by tail-cuff plethysmography. 24-hr water consumption was monitored, and 24-hour urine samples were collected at days 7, 11, 15, and 19 of pregnancy, or at corresponding times in the control group. Aliquots of urine (0.5 ml) were extracted on C18 reverse-phase columns to measure the concentrations of MBG.

The transport activity of sodium pump was estimated in the rings of thoracic aorta by measurement of MBG-sensitive $^{86}$Rb uptake. Vascular rings 2-2.5 mm diameter were equilibrated for 60 minutes at 32° C. in 5 ml flasks in a medium containing (in mM): NaCl 120, KCl 4, $CaCl_2$ 2.5, $MgCl_2$ 2.0, $NaH_2PO_4$ 1.1, $NaHCO_3$ 24, and glucose 5.6, gassed with 95% $O_2$ and 5% $CO_2$ at pH 7.4. $^{86}$Rb (0.1 µCi/sample, NEN Life Science Products, Boston, Mass.) was then added, and the vessels were incubated for 60 minutes at 37° C. in duplicate, in the absence and presence of 1 mM MBG. The samples were then rinsed three times in ice-cold medium, blotted with filter paper, weighed, and counted in a gamma counter (Cherenkov Radiation). Total $^{86}$Rb uptake was determined on a wet weight basis. The activity of the sodium pump was measured as the difference between the total uptake of $^{86}$Rb and the uptake in the presence of 1 mM MBG and expressed in µmol of $^{86}$Rb per 1 gram of wet weight of tissue per 1 minute.

The effect of the 3E9 mAb on thoracic aorta $Na^+/K^+$-ATPase activity was compared in a subset of pregnant rats following NaCl supplementation for 7 days. A single intraperitoneal administration of the 3E9 mAb (0.34 mg/kg) was associated with an increase in $Na^+/K^+$-ATPase activity: activity before=106±5, activity after =126±4.

Example 8

Effects of Anti-Marinobufagenin Antibodies on Uremic Cardiomyopathy

This example demonstrates that anti-marinobufagenin antibodies reduce pathology associated with experimental uremic cardiomyopathy.

Male, Sprague-Dawley were use in this study. Rats subjected to sham surgery and no MBG infusion or partial nephrectomy were referred to as Sham (n=18). Rats subjected to partial nephrectomy (n=8), as well as those who received control immunization against BSA and partial nephrectomy (n=12), were very similar with respect to functional and biochemical analysis and were, therefore, pooled into one group and referred to as PNx (n=20). MBG-infused rats were referred to as MBG (n=20). Rats immunized against MBG-BSA conjugate before partial nephrectomy were referred to as PNx-IM (n=18).

MBG was isolated from toad (*Bufo Marinus*) venom. The isolated MBG was >99% pure based on highperformance liquid chromatography and mass spectroscopy analysis. MBG was infused for a period of 4 weeks at 10 μg/kg per day with an osmotic minipump (Alzet Model 2004, Durect Corp).

Partial nephrectomy (five-sixth nephrectomy) was induced by removal of the right kidney and selective infarction of two-thirds of the left kidney with silk ligatures.

Rats were immunized with an MBG-BSA conjugate and subjected to partial nephrectomy. The immunization schedule was 3 weekly injections (250 μg/kg per week SQ) in complete Freund's adjuvant before the partial nephrectomy with a last boost at the time of surgery. This regimen previously induced high titers of antibodies (>1:10 000) to MBG. The antibodies produced had high affinity to MBG and very little cross-reactivity (<<1%) to aldosterone, ouabain, digoxin, bufalin, and progesterone.

BP was measured once a week by the tail-cuff method in conscious, restrained rats with equipment made by IITC, Inc (Amplifier model 229, Monitor model 31, Test chamber Model 306; IITC Life Science). Before sacrifice at 4 weeks, animals had ventricular pressures determined by placement of a 2F Millar Microtip Catheter Transducer (Millar Instruments Inc) into the left ventricle through a carotid insertion. Hemodynamic data were acquired at 500 Hz and stored electronically using a BioPac MP110 acquisition system and AcqKnowledge 4.7.3 software (BIOPAC Systems, Inc). The values of left ventricular end-diastolic pressure (LVEDP), systolic pressure, developed pressure, maximal velocity of rise or fall in pressure (dP/dt) and the time constant for isovolumic relaxation were determined using standard methods. At the end of 4 weeks, 2D and M-mode echocardiographic studies were performed using a Philips Sonos 5500 cardiovascular ultrasound imaging system (Philips Medical Systems) equipped with a 15 MHz linear transducer. Parasternal long-axis and short-axis views were obtained.

MBG and ouabain-like compound (OLC) in plasma and urine was determined at 4 weeks after extraction with C-18 columns.

At the time of sacrifice, left ventricles were quickly dissected out, frozen in liquid nitrogen, and stored at −80° C. until further analysis. Western blot analysis was performed using SDS-PAGE gels (Ready Gel, BioRad).

Total protein carbonyl concentration of both the plasma and left ventricular homogenate was determined by ELISA using the Zentech PC Test kit (Northwest Life Science Specialties). Total plasma malondialdehyde was measured spectrophotometrically using the Bioxytech MDA-586 kit (Oxis Research).

To measure sarcoplasmic reticulum calcium ATPase activity, which is predominantly SERCA2a activity in left ventricles of rat cardiac tissue, the method of Simonides and van Hardeveld (Simonides and van Hardeveld, *Anal. Biochem.* 191:321-331, 1990) was used with minor modifications.

Hematocrit was measured from whole blood collected in heparinized capillary tubes and spun on a microhematocrit centrifuge (Fisher Scientific). Plasma creatinine was determined spectrophotometrically with a colorimetric end point assay (Teco Diagnostics). Plasma aldosterone levels were measured by ELISA (Cayman). Plasma parathyroid hormone was assayed using the Rat Intact PTH ELISA kit (Immutopics). All of the analyses were performed on blood collected upon sacrifice at 4 weeks.

Rats with partial nephrectomy had substantial increases in plasma [MBG] and urinary MBG excretion rates ($U_{MBG}V$) at 4 weeks after surgery compared with control rats (Table V). Infusion of MBG alone induced comparable increases in plasma [MBG] and $U_{MBG}V$ as partial nephrectomy. Immunization against MBG-BSA in partial nephrectomy animals was associated with a decrease in UMBGV compared with partial nephrectomy alone. Neither plasma or urine OLC levels were different between sham and partial nephrectomy, nor was there a significant effect of either MBG supplementation or immunization against MBG on plasma or urine OLC levels (Table V).

TABLE V

Effects of MBG on Various Biochemical and Functional Prameters

| Variable | Sham | Pnx | MGB | PNx-IM |
| --- | --- | --- | --- | --- |
| Plasma [MBG], pmol/L | 359 ± 16 | 564 ± 36 | 546 ± 34 | 430 ± 36 |
| Urinary MBG excretion ($U_{MBG}V$), pmol/24 h | 31.3 ± 2.3 | 60.2 ± 4.5 | 49.1 ± 3.5 | 44.7 ± 4.0 |
| Plasma [OLC], pmol/L | 428 ± 53 | 437 ± 43 | 493 ± 41 | 528 ± 38 |
| Urinary OLC excretion ($U_{OLC}V$), pmol/24 h | 11.7 ± 1.5 | 11.4 ± 1.9 | 10.6 ± 0.9 | 11.1 ± 1.1 |
| Plasma creatinine, mg/dL | 0.30 ± 0.03 | 0.95 ± 0.12 | 0.52 ± 0.07 | 0.95 ± 0.13 |
| Hematocrit, % | 44.5 ± 0.8 | 38.8 ± 1.3 | 44.6 ± 0.9 | 41.1 ± 0.7 |
| Plasma parathyroid hormone, pg/mL | 41 ± 6 | 126 ± 17 | 41 ± 9 | 140 ± 26 |
| Plasma aldosterone, pg/mL | 191 ± 55 | 1780 ± 371 | 322 ± 38 | 2207 ± 474 |

Analyses performed 4 weeks after sham operation, partial nephrectomy, MGB infusion, or immunization prior to partial nephrectomy.

Partial nephrectomy led to marked increases in plasma creatinine and decreases in hematocrit, which were not affected by immunization (Table V). MBG infusion to sham-operated rats did not significantly alter either of these measurements. Partial nephrectomy induced considerable increases in plasma aldosterone and parathyroid hormone concentrations in the plasma compared with sham-operated controls (Table V). MBG administration did not significantly increase these hormone concentrations in the plasma compared with the sham-operated controls, whereas immunization against MBG did not alter these hormone concentrations compared with partial nephrectomy alone. Rats with partial nephrectomy had systemic and cardiac oxidant stress as indicated by increases in both plasma and left ventricular tissue carbonylated proteins, as well as increases in plasma malondialdehyde compared with control rats, whereas MBG infusion alone only produced statistically significant increases in plasma carbonylation (Table VI). Immunization against MBG in partial nephrectomy animals substantially reduced oxidant stress compared with partial nephrectomy alone (Table VI).

TABLE VI

MGB Induces Oxidative Stress in Vivo

| Variable | Sham | Pnx | MBG | Pnx-IM |
|---|---|---|---|---|
| Plasma carbonylated protein pmol/mg protein | 171 ± 9 | 340 ± 20 | 378 ± 15 | 241 ± 24 |
| Left ventricular carbonylated protein pmol/mg protein | 387 ± 23 | 541 ± 41 | 505 ± 22 | 393 ± 39 |
| Plasma total malondialdehyde, nm | 399 ± 17 | 571 ± 49 | 474 ± 41 | 428 ± 34 |

Analyses performed 4 weeks after sham operation, partial nephrectomy, MGB infusion, or immunization prior to partial nephrectomy.

Partial nephrectomy was associated with marked increases in systolic BP during the 4 weeks of observation. MBG infusion alone produced some increases in BP compared with control, but these increases were less than that observed with partial nephrectomy alone. Immunization against MBG did not significantly attenuate the increases in BP seen with partial nephrectomy. Echocardiographic imaging studies demonstrated that partial nephrectomy animals had considerable increases in left ventricular wall thickness compared with controls. Left ventricular end-diastolic and end-systolic volumes were markedly reduced in the partial nephrectomy animals, and the calculated fractional shortening (FS) was also substantially increased. MBG infusion was not associated with significant changes in wall thickness, chamber size, or FS compared with sham-treated controls. Immunization against MBG ameliorated the echocardiographic changes noted with partial nephrectomy.

After 4 weeks, the animals were anesthetized, and a Millar catheter was introduced into the left ventricle to measure left ventricular hemodynamics. Partial nephrectomy surgery induced substantial increases in maximal velocity of rise in pressure (dP/dt) compared with controls. However, diastolic function was impaired as assessed by the ratio of maximal positive dP/dt to maximal negative dP/dt, an increase in LVEDP, as well as the time constant for left ventricular isovolumic relaxation. A similar pattern was noted in the rats subjected to MBG infusion, but only the changes in LVEDP and time constant for isovolumic relaxation achieved statistical significance. Immunization against MBG in partial nephrectomy animals considerably attenuated the changes in maximal positive dP/dt, the ratio of maximal positive dP/dt to negative dP/dt, LVEDP, and the time constant for ventricular relaxation seen with partial nephrectomy.

Rats subjected to partial nephrectomy had marked increases in heart weight compared with control animals. Although MBG infusion also resulted in significant increases in heart weight, these increases were less than that seen with partial nephrectomy. Partial nephrectomy was associated with activation of extracellular signal regulated kinase and Src, upregulation of skACT, as well as downregulation of both the $\alpha 1$ and $\alpha 2$ isoform of the Na/K-ATPase and SERCA2a.

SERCA enzymatic activity was also decreased in partial nephrectomy-treated animals. A similar pattern of changes in protein expression was noted in rats subjected to MBG infusion. Immunization against MBG prevented or attenuated the increases in cardiac size, activation of ERK and Src, upregulation of skACT, as well as the downregulation of $\alpha 2$ Na/K-ATPase and SERCA2a expression and SERCA function with partial nephrectomy. Partial nephrectomy resulted in marked increases in cardiac fibrosis as assessed by either semiquantitative grade or morphometric analysis. MBG infusion produced similar histological changes as partial nephrectomy. Immunization against MBG markedly attenuated the histological changes seen with partial nephrectomy. Partial nephrectomy was associated with marked increases in fibronectin, whereas immunization against MBG markedly attenuated the changes in fibronectin.

Example 9

Effects of the 3E9, 4G4 and 4H2 mAbs on Myocardial Fibrosis

This example demonstrates the in vivo effect of the 3E9, 4G4 and 4H2 mAbs on myocardial fibrosis in rats with angiotensin II induced hypertension.

Angiotensin II infusion results in a reproducible increase in systolic blood pressure, concentric left ventricular (LV) hypertrophy, associated with reactive fibrosis and myocyte hypertrophy, and MBG production (Capers et al., *Hypertension* 30:1397-1402, 1997, Kuwahara et al., *Hypertension* 43:739, 2004, Fedorova et al., *J. Hypertension* 23:1515-1523, 2005).

Infusion of Angiotensin II rats to induce myocardial fibrosis. For the angiotensin II-treated animals, angiotensin II is dissolved in a solution of 0.15 mol/L NaCl and 0.01 mol/L acetic acid. Control animals are either are infused with vehicle or nothing. Systolic blood pressure is measured at baseline and before death with a tail-cuff sphygmomanometer.

The effect of the anti-MBG 3E9, 4G4 and 4H2 mAbs on myocardial fibrosis is determined by intravenously treating angiotensin treated rat with anti-MBG mAbs and comparison with control rats not treated with the anti-MBG mAbs. Treatment with anti-MBG mAbs attenuates concentric left ventricular (LV) hypertrophy, and myocardial fibrosis.

While this disclosure has been described with an emphasis upon preferred embodiments, it will be obvious to those of ordinary skill in the art that variations of the preferred embodiments may be used and it is intended that the disclosure may be practiced otherwise than as specifically described herein. Accordingly, this disclosure includes all modifications encompassed within the spirit and scope of the disclosure as defined by the claims below.

We claim:

1. A hybridoma cell line deposited with the American Type Culture Collection under ATCC accession numbers PTA-6724 (3E9 hybridoma), PTA-6725 (4G4 hybridoma), or PTA-6788 (4H2 hybridoma).

2. A monoclonal antibody produced by any one of the hybridoma cell lines of claim 1, or a marinobufagenin-binding fragment thereof.

3. The monoclonal antibody of claim 2, wherein the monoclonal antibody or fragment thereof is labeled with a detectable agent.

4. The monoclonal antibody of claim 3, wherein the detectable agent comprises an electron-dense compound, an enzyme, a fluorochrome, a hapten, or a radioisotope.

5. A method of detecting the presence of marinobufagenin (MBG) in a biological sample, comprising:
    contacting the sample with the monoclonal antibody of claim 2; and
    detecting the binding of the monoclonal antibody with the sample, thereby detecting MBG in the sample.

6. The method of claim 5, wherein the monoclonal antibody is labeled with a detectable agent to detect marinobufagenin in the sample.

7. The method of claim 5, wherein detecting marinobufagenin in the sample comprises contacting the sample with a second antibody that specifically binds the monoclonal antibody.

8. The method of claim 7, wherein the second antibody is labeled with a detectable agent.

9. A method of diagnosing cardiovascular disease associated with increased MBG levels in a subject, comprising:
    contacting a biological sample from the subject with the monoclonal antibody of claim 2; and
    detecting the binding of the monoclonal antibody of claim 2 with MBG in the sample, wherein an increase in detected MBG in the sample as compared to detected MBG in a sample from another subject without cardiovascular disease associated with increased MBG levels is indicative of the diagnosis of cardiovascular disease associated with increased MBG levels in the subject.

10. The method of claim 9, wherein the method is a method of diagnosing hypertension.

11. The method of claim 9, wherein the method is a method of diagnosing essential hypertension.

12. The method of claim 9, wherein the method is a method of diagnosing preeclampsia or eclampsia.

13. The method of claim 9, wherein the method is a method of diagnosing, myocardial fibrosis.

14. The method of claim 9, wherein the method is a method of diagnosing uremic cardiomyopathy.

15. The method of claim 9, wherein the monoclonal antibody is labeled with a detectable agent, and detecting the binding comprises detecting the detectable agent.

16. A method of treating or inhibiting cardiovascular disease associated with increased MBG levels in a subject, comprising:
    selecting a subject who has cardiovascular disease associated with increased MBG levels; and
    administering to the subject a therapeutically effective amount of the monoclonal antibody of claim 2 in a pharmaceutically acceptable carrier to treat or inhibit the cardiovascular disease associated with increased MBG levels.

17. The method of claim 16, wherein the subject is a human subject.

18. The method of claim 16, wherein selecting a subject who has cardiovascular disease comprises selecting a subject who has hypertension.

19. The method of claim 18, wherein selecting a subject who has hypertension comprises selecting a subject who has preeclampsia or eclampsia.

20. The method of claim 18, wherein selecting a subject who has hypertension comprises selecting a subject who has myocardial fibrosis.

21. The method of claim 16, wherein the cardiovascular disease is uremic cardiomyopathy.

22. The method of claim 16, wherein the cardiovascular disease is myocardial fibrosis.

23. The method of claim 16, further comprising administering to the subject a therapeutically effective amount of an angiotensin-converting enzyme inhibitor, an angiotensin receptor blocker, a diuretic, a calcium channel blocker, an alpha-adrenoceptor blocker, an endothelin-1 receptor blocker, an organic nitrate, a protein kinase C inhibitor, or a combination thereof.

24. A humanized antibody that specifically binds marinobufagenin, wherein the humanized antibody comprises the complementary determining regions (CDRs) of the antibody produced by any one of the hybridoma cell lines of claim 1 and a human framework region.

25. A composition comprising the monoclonal antibody of claim 2.

26. The composition of claim 25, further comprising a pharmaceutically acceptable carrier.

27. The composition of claim 26, wherein the pharmaceutically acceptable carrier comprises saline.

28. The monoclonal antibody of claim 2, wherein the antibody is conjugated to a carrier protein.

29. A substrate comprising the monoclonal antibody of claim 2.

30. The substrate of claim 29, wherein the substrate is a bead.

31. A monoclonal antibody produced by the 3E9 hybridoma cell line of claim 1 or a marinobufagenin-binding fragment thereof.

32. A monoclonal antibody produced by the 4G4 hybridoma cell line of claim 1 or a marinobufagenin-binding fragment thereof.

33. The method of claim 5, wherein the biological sample comprises a blood or urine sample.

34. The method of claim 5, wherein the biological sample comprises plasma.

35. The method of claim 9, wherein the biological sample comprises plasma.

36. The method of claim 9, wherein the subject is a mammalian subject.

37. The method of claim 9, wherein the subject is a human.

38. A method of diagnosing hypertension, uremic cardiomyopathy, or preeclampsia in a mammalian subject, comprising:
    contacting a biological sample from the mammalian subject with the monoclonal antibody of claim 2; and
    detecting the binding of the monoclonal antibody with MBG in the sample, wherein an increase in detected MBG in the sample as compared to detected MBG in a sample from another mammalian subject without hypertension, uremic cardiomyopathy or preeclampsia is indicative of the diagnosis of hypertension, uremic cardiomyopathy or preeclampsia in the mammalian subject.

39. The method of claim 38, wherein the biological sample comprises a blood or urine sample.

40. The method of claim 38, wherein the mammalian subject is a human.

41. The method of claim 38, wherein the monoclonal antibody is produced by a hybridoma deposited with the American Type Culture Collection under ATCC accession number PTA-6725 (4G4 hybridoma).

42. A method of reducing arterial blood pressure in a mammalian subject, comprising:
    selecting a mammalian subject who has hypertension; and
    administering to the mammalian subject a therapeutically effective amount of the monoclonal antibody of claim 2 to reduce the arterial blood pressure in the mammalian subject.

43. The method of claim 42, wherein the monoclonal antibody is produced by a hybridoma deposited with the American Type Culture Collection under ATCC accession number PTA-6724 (3E9 hybridoma).

44. The method of claim 42, wherein the mammalian subject is a human.

45. The method of claim 42, wherein the mammalian subject who has hypertension has preeclampsia.

46. The method of claim 42, wherein the mammalian subject who has hypertension has myocardial fibrosis.

47. The method of claim 42, wherein the mammalian subject who has hypertension has uremic cardiomyopathy.

48. A method of increasing $Na^+/K^+$-ATPase activity in a mammalian subject, comprising:
    selecting a mammalian subject who has hypertension; and
    administering to the mammalian subject a therapeutically effective amount of the monoclonal antibody of claim 2 to increase the $Na^+/K^+$-ATPase activity in the mammalian subject.

49. The method of claim 48, wherein the monoclonal antibody is produced by a hybridoma deposited with the American Type Culture Collection under ATCC accession number PTA-6724 (3E9 hybridoma.

50. The method of claim 48, wherein the mammalian subject is a human.

51. The method of claim 48, wherein the mammalian subject who has hypertension has preeclampsia.

52. The method of claim 48, wherein the mammalian subject who has hypertension has myocardial fibrosis.

53. The method of claim 48, wherein the mammalian subject who has hypertension has uremic cardiomyopathy.

54. A composition comprising the hybridoma cell line of claim 1.

55. A method of detecting the presence of marinobufagenin (MBG) in a biological sample, comprising:
    contacting the sample with the humanized antibody of claim 24; and
    detecting the binding of the humanized antibody with the sample, thereby detecting MBG in the sample.

56. A method of diagnosing cardiovascular disease associated with increased MBG levels in a subject, comprising:
    contacting a biological sample from the subject with the humanized antibody of claim 24; and
    detecting the binding of the humanized antibody of claim 24 with MBG in the sample, wherein an increase in detected MBG in the sample as compared to detected MBG in a sample from another subject without cardiovascular disease associated with increased MBG levels is indicative of the diagnosis of cardiovascular disease associated with increased MBG levels in the subject.

57. A method of treating or inhibiting cardiovascular disease associated with increased MBG levels in a subject, comprising:
    selecting a subject who has cardiovascular disease associated with increased MBG levels; and
    administering to the subject a therapeutically effective amount of the humanized antibody of claim 24 in a pharmaceutically acceptable carrier to treat or inhibit the cardiovascular disease associated with increased MBG levels.

\* \* \* \* \*

UNITED STATES PATENT AND TRADEMARK OFFICE
CERTIFICATE OF CORRECTION

PATENT NO.        : 8,038,997 B2
APPLICATION NO.   : 11/993309
DATED             : October 18, 2011
INVENTOR(S)       : Bagrov et al.

It is certified that error appears in the above-identified patent and that said Letters Patent is hereby corrected as shown below:

Column 5, line 37, "404" should read -- 4G4 --.

Column 5, line 52, "cardiomyopathy)" should read -- cardiomyopathy). --.

Column 6, line 46, "MBG MBG" should read -- MBG, MBG --.

Column 8, line 40, "hypertrophy. with" should read -- hypertrophy with --.

Column 12, line 13 "amount of an a" should read -- amount of a --.

Column 18, line 15, "Handbook;" should read -- Handbook, --.

Column 19, lines 54-55, "parentally" should read -- parenterally --.

Column 21, line 50, "administration a" should read -- administration of a --.

Column 22, line 24, "embodiment, MGB" should read -- embodiment, the composition includes MGB --.

Column 22, line 25, "ergent" should read -- agent --.

Column 22, line 31, "polysorbate, 80" should read -- polysorbate 80 --.

Column 22, line 32, "ethanediyl;" should read -- ethanediyl); --.

Column 23, line 1, "agent" should read -- agents --.

Column 25, line 67, "4112" should read -- 4H2 --.

Column 27, line 6, "$Na^+/K^+ATPase$" should read -- $Na^+/K^+$ - ATPase --.

Column 28, line 31, "Day 5 pregnant and on nonpregnant" should read -- Five-days pregnant and nonpregnant --.

Column 29, line 12, "use in" should read -- used in --.

Column 29, line 36, "10 000" should read -- 10,000 --.

Column 30, line 44, "UMBGV" should read -- $U_{MBG}V$ --.

Column 30, Table V, "Prameters" should read -- Parameters --.

Column 30, Table V, "MGB" should read -- MBG --.

Signed and Sealed this
Twentieth Day of March, 2012

David J. Kappos
*Director of the United States Patent and Trademark Office*

Column 31, Table VI, "MGB" should read -- MBG --.

Column 32, line 10, "Na/K -ATPase" should read -- $Na^+/K^+$ - ATPase --.

Column 32, lines 18-19, "Na/K - ATPase" should read -- $Na^+/K^+$ - ATPase --.

Column 32, line 49, "are either are" should read -- are either --.

Column 32, line 56, "rat" should read -- rats --.

Column 33, line 50 (claim 13), "diagnosing, myocardial" should read
-- diagnosing myocardial --.

Column 35, line 36 (claim 49), "hybridoma." should read -- hybridoma). --.